US012727975B2

(12) United States Patent
Tanaka

(10) Patent No.: US 12,727,975 B2
(45) Date of Patent: Sep. 8, 2026

(54) THREE-DIMENSIONAL SCANNER AND CONTROL METHOD

(71) Applicant: J. MORITA MFG. CORP., Kyoto (JP)

(72) Inventor: Tsuyoshi Tanaka, Kyoto (JP)

(73) Assignee: J. MORITA MFG. CORP., Kyoto (JP)

(*) Notice: Subject to any disclaimer, the term of this patent is extended or adjusted under 35 U.S.C. 154(b) by 150 days.

(21) Appl. No.: 18/671,480

(22) Filed: May 22, 2024

(65) Prior Publication Data

US 2024/0390119 A1 Nov. 28, 2024

(30) Foreign Application Priority Data

May 24, 2023 (JP) ................................ 2023-085378

(51) Int. Cl.

| | |
|---|---|
| ***A61C 9/00*** | (2006.01) |
| ***A61B 1/00*** | (2006.01) |
| ***A61B 1/24*** | (2006.01) |
| ***G02B 26/08*** | (2006.01) |
| ***G02B 26/10*** | (2006.01) |
| ***H04N 23/959*** | (2023.01) |

(52) U.S. Cl.

CPC ........ *A61C 9/0066* (2013.01); *A61B 1/00172* (2013.01); *A61B 1/24* (2013.01); *G02B 26/0875* (2013.01); *G02B 26/10* (2013.01); *H04N 23/959* (2023.01)

(58) Field of Classification Search

CPC .................... A61B 5/4547; G06T 2207/30036

See application file for complete search history.

(56) References Cited

U.S. PATENT DOCUMENTS

| | | | |
|---|---|---|---|
| 11,060,852 | B2 | 7/2021 | Sorimoto |
| 2005/0283065 | A1 | 12/2005 | Babayoff |
| 2006/0001739 | A1 | 1/2006 | Babayoff |
| 2008/0024768 | A1 | 1/2008 | Babayoff |
| 2009/0153858 | A1 | 6/2009 | Babayoff |
| 2010/0208275 | A1 | 8/2010 | Babayoff |
| 2012/0075425 | A1 | 3/2012 | Thiel |
| 2012/0092678 | A1 | 4/2012 | Babayoff |

(Continued)

FOREIGN PATENT DOCUMENTS

| | | | |
|---|---|---|---|
| CN | 103491897 | B | 1/2016 |
| JP | 2012-518445 | A | 8/2012 |

(Continued)

OTHER PUBLICATIONS

Extended European Search Report issued Oct. 18, 2024 in European Patent Application No. 24175196.5.

(Continued)

*Primary Examiner* — Thanh Luu

(74) *Attorney, Agent, or Firm* — Oblon, McClelland, Maier & Neustadt, L.L.P.

(57) ABSTRACT

A three-dimensional scanner includes a lens, imaging circuitry that obtains an image of an object located at a focal position of the lens, a lens driver that drives the lens to make reciprocating motion in a linear direction, obtaining circuitry that obtains geometrical data representing a surface geometry based on an image taken by the imaging circuitry, and lens controller circuitry that controls the lens driver to change an amplitude of reciprocating motion of the lens based on the geometrical data obtained by the obtaining circuitry.

18 Claims, 14 Drawing Sheets

(56) References Cited

U.S. PATENT DOCUMENTS

2013/0027515 A1 1/2013 Vinther et al.
2013/0070985 A1 3/2013 Babayoff
2013/0243284 A1 9/2013 Babayoff
2014/0022352 A1* 1/2014 Fisker ........................ G06T 5/50 348/46
2014/0119622 A1 5/2014 Babayoff
2015/0022824 A1 1/2015 Babayoff
2015/0297329 A1 10/2015 Babayoff
2016/0295191 A1 10/2016 Babayoff
2019/0174110 A1 6/2019 Babayoff
2019/0191141 A1 6/2019 Fisker et al.
2019/0230336 A1 7/2019 Babayoff
2019/0238820 A1 8/2019 Babayoff
2019/0281272 A1 9/2019 Babayoff
2020/0186777 A1 6/2020 Babayoff
2020/0236336 A1 7/2020 Babayoff
2021/0152805 A1 5/2021 Babayoff
2021/0152806 A1 5/2021 Babayoff
2021/0160471 A1 5/2021 Fisker et al.
2021/0186667 A1 6/2021 Abu-Tarif et al.
2021/0389549 A1* 12/2021 Berner ..................... G02B 7/04
2023/0224446 A1 7/2023 Babayoff
2024/0289954 A1* 8/2024 Lee ...................... A61B 1/0005

FOREIGN PATENT DOCUMENTS

JP 2016-534334 A 11/2016
JP 2019-180881 A 10/2019
JP 2020-034487 A 3/2020
WO WO 2015/015289 A2 2/2015

OTHER PUBLICATIONS

Japanese Notice of Reasons for Refusal issued Sep. 2, 2025 with English translation, 8 pgs.

* cited by examiner

THREE-DIMENSIONAL SCANNER
100
50
POWER SUPPLY
45
40
CONTROL DEVICE
41
COMPUTING UNIT
42
STORAGE UNIT
43
CONTROL PROGRAM
OPTICAL MEASUREMENT UNIT
30
70
HANDPIECE
CONNECTION PORTION
20
10
PROBE
OBJECT
99

HANDPIECE
70
71
75
77
10
66
81
501
72
500
91
502
Z
X
Y 80
85a(85)
51a
77
52a
55a
81
56a(60a)
57a(60a)
56b(60b)
57b(60b)
52b
51b
85b(85)
Z
Y
X 80
53a
(S POLE)
53a
(N POLE)
51a
52a
85a(85)
81
56a(60a)
55b
55a
L
57a(60a)
85b(85)
52b
51b
53b
(N POLE)
53b
(S POLE)
F
Z
Y
X

70
DEPTH OF FIELD
IMAGE CANNOT
BE TAKEN
99

70
DEPTH OF FIELD
EXTRA IMAGING
99

40
LENS CONTROLLER
402
OBTAINING UNIT
401
70
70
OUTPUT DATA
(DRIVE CURRENT)
GEOMETRICAL DATA
(THREE-DIMENSIONAL DATA,
COLOR DATA)

70
DEPTH OF FIELD
IMAGE CAN
BE TAKEN
99

70
DEPTH OF FIELD
NO EXTRA IMAGING
99

70
GEOMETRICAL DATA
OBTAINING UNIT
411
40
413
ESTIMATOR
414
ESTIMATION MODEL (TRAINED MODEL)
NEURAL NETWORK
PARAMETER (WEIGHT COEFFICIENT, CRITERION VALUE)
441
442
ESTIMATION DATA
LENS CONTROLLER
412
OUTPUT DATA (DRIVE CURRENT)
70

FIG.14

| PATTERN | GEOMETRICAL DATA | ESTIMATION DATA | OUTPUT DATA |
|---|---|---|---|
| A | TWO-DIMENSIONAL DATA | DEPTH OF FIELD (RATIO OF TOOTH) | DRIVE CURRENT |
| B | TWO-DIMENSIONAL DATA | RESULT OF IDENTIFICATION OF OBJECT | DRIVE CURRENT |
| C | TWO-DIMENSIONAL DATA | DRIVE CURRENT | DRIVE CURRENT |
| D | TWO-DIMENSIONAL DATA + COLOR DATA | DEPTH OF FIELD (RATIO OF TOOTH) | DRIVE CURRENT |
| E | TWO-DIMENSIONAL DATA + COLOR DATA | RESULT OF IDENTIFICATION OF OBJECT | DRIVE CURRENT |
| F | TWO-DIMENSIONAL DATA + COLOR DATA | DRIVE CURRENT | DRIVE CURRENT |
| G | THREE-DIMENSIONAL DATA | DEPTH OF FIELD (RATIO OF TOOTH) | DRIVE CURRENT |
| H | THREE-DIMENSIONAL DATA | RESULT OF IDENTIFICATION OF OBJECT | DRIVE CURRENT |
| I | THREE-DIMENSIONAL DATA | DRIVE CURRENT | DRIVE CURRENT |
| J | THREE-DIMENSIONAL DATA + COLOR DATA | DEPTH OF FIELD (RATIO OF TOOTH) | DRIVE CURRENT |
| K | THREE-DIMENSIONAL DATA + COLOR DATA | RESULT OF IDENTIFICATION OF OBJECT | DRIVE CURRENT |
| L | THREE-DIMENSIONAL DATA + COLOR DATA | DRIVE CURRENT | DRIVE CURRENT |

THREE-DIMENSIONAL SCANNER AND CONTROL METHOD

CROSS REFERENCE TO RELATED APPLICATIONS

This nonprovisional application is based on Japanese Patent Application No. 2023-085378 filed with the Japan Patent Office on May 24, 2023, the entire contents of which are hereby incorporated by reference.

BACKGROUND

Field

The present disclosure relates to a three-dimensional scanner configured to obtain three-dimensional data of a surface geometry of an object with a focus method and a control method of controlling the three-dimensional scanner.

Description of the Background Art

A three-dimensional scanner that scans a surface geometry of an object such as a tooth and a soft tissue in a mouth cavity to obtain three-dimensional data of the surface geometry has conventionally been known. For example, Japanese Patent Laying-Open No. 2019-180881 discloses a three-dimensional scanner that obtains three-dimensional data of a surface geometry of an object by projecting on the object, light that has passed through a lens while the lens is caused to make reciprocating motion in a linear direction and detecting light reflected at the object.

SUMMARY

In the three-dimensional scanner disclosed in Japanese Patent Laying-Open No. 2019-180881, depending on an amplitude of reciprocating motion of the lens, a depth of field which is a range of a focal position of light that passes through the lens may not be stable. When the depth of field is smaller than an appropriate value, the range that can be imaged in one imaging is excessively narrow, which makes imaging by a user difficult and also increases a time period for imaging. In addition, since the number of times of operation to put together imaged portions increases, accuracy of obtained three-dimensional data is lowered. When the depth of field is larger than the appropriate value, on the other hand, the range that can be imaged in one imaging is excessively large, which may result in imaging of an unnecessary portion which is not a target of imaging. Therefore, computing load for erasure of the unnecessary portion is imposed, and accordingly a computing speed is lowered and an amount of heat generation also increases. A frame rate of an imaging unit may be lowered in order to suppress the amount of heat generation. Lowering in frame rate, however, lowers accuracy of obtained three-dimensional data.

The present disclosure was made to solve the problem above, and an object thereof is to provide a technique that enables setting of a depth of field to an appropriate value in obtaining three-dimensional data of a surface geometry of an object.

A three-dimensional scanner according to the present disclosure is configured to obtain three-dimensional data of a surface geometry of an object with a focus method. The three-dimensional scanner includes a lens, an imaging unit configured to take an image of the object located at a focal position of the lens, a lens driver configured to drive the lens to make reciprocating motion in a linear direction, an obtaining unit configured to obtain geometrical data representing the surface geometry based on an image taken by the imaging unit, and a lens controller configured to control the lens driver to change an amplitude of reciprocating motion of the lens based on the geometrical data obtained by the obtaining unit.

A control method according to the present disclosure is a method of controlling a three-dimensional scanner configured to obtain three-dimensional data of a surface geometry of an object with a focus method. The control method includes, as processing to be performed by a computer, taking an image of the object located at a focal position of a lens provided in the three-dimensional scanner, driving the lens to make reciprocating motion in a linear direction, obtaining geometrical data representing the surface geometry based on an image taken in the taking an image, and changing an amplitude of reciprocating motion of the lens based on the geometrical data obtained in the obtaining geometrical data.

The foregoing and other objects, features, aspects and advantages will become more apparent from the following detailed description when taken in conjunction with the accompanying drawings.

BRIEF DESCRIPTION OF THE DRAWINGS

FIG. 14 is a diagram for explaining geometrical data, estimation data, and output data in the three-dimensional scanner according to the modification.

DESCRIPTION OF THE EMBODIMENTS

Embodiment

An embodiment of the present disclosure will be described with reference to the drawings.

[Configuration of Three-Dimensional Scanner]

Figure 1:
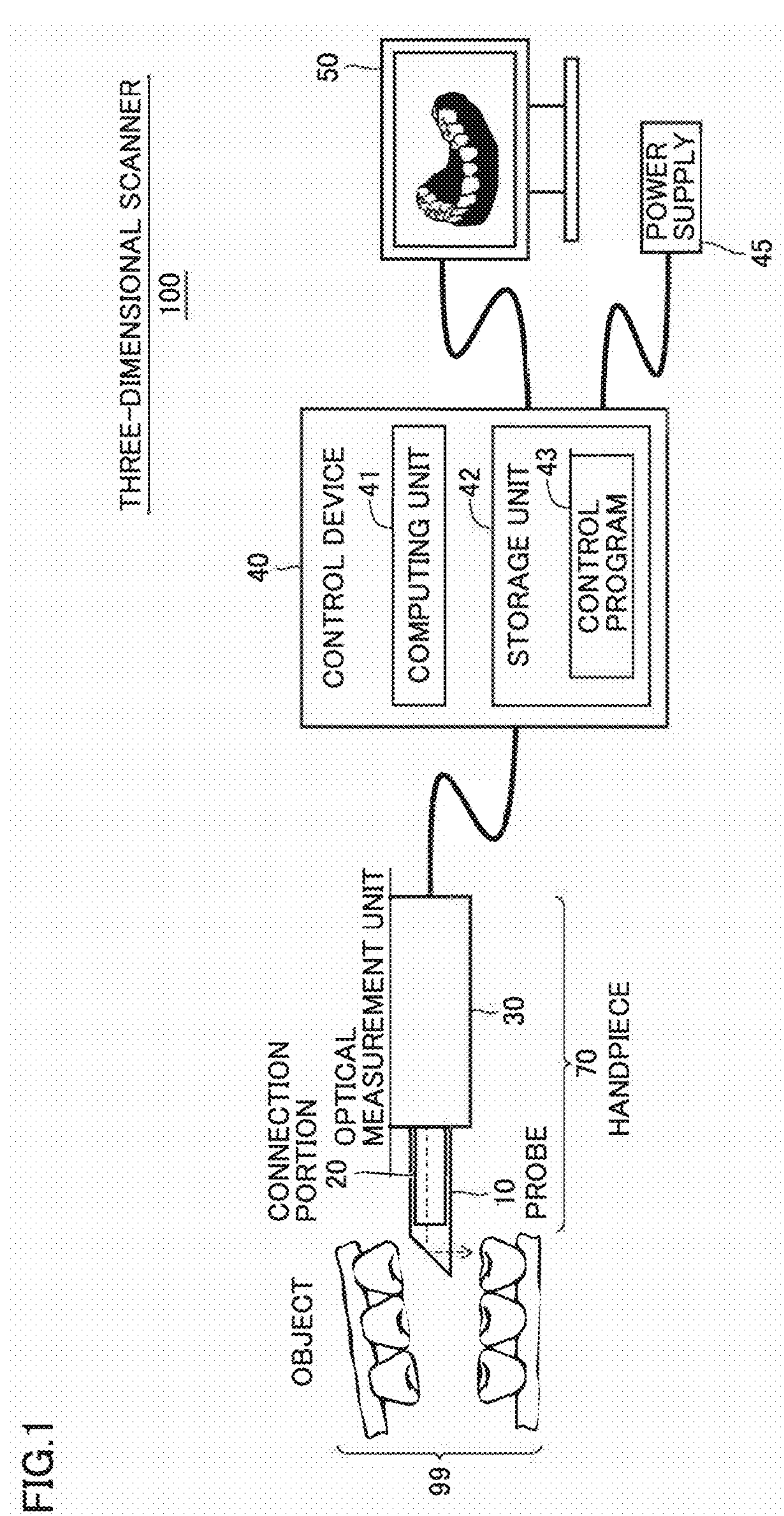
FIG. 1 is a diagram showing a configuration of a three-dimensional scanner according to an embodiment.

FIG. 1 is a diagram showing a configuration of a three-dimensional scanner 100 according to an embodiment. Three-dimensional scanner 100 is an intra oral scanner (IOS) that obtains three-dimensional data of a surface geometry of an object 99 such as a tooth and a soft tissue in a mouth cavity by scanning the surface geometry. The three-dimensional data includes positional information (a coordinate along axes in a vertical direction, a lateral direction, and a height direction) of each point in a group of points (a plurality of points) representing the surface geometry of object 99. Three-dimensional scanner 100 can also obtain color data indicating a color of each point in the group of points (the plurality of points) representing the surface geometry of object 99, together with the three-dimensional data.

Three-dimensional scanner 100 according to the embodiment is applicable also to medical care in every medical department such as an ophthalmology department, an otorhinolaryngology department, a radiology department, internal medicine, surgery, and a veterinary department, without being limited to dentistry. For example, three-dimensional scanner 100 according to the embodiment is not limited to the intra oral scanner but is applicable also to another similarly configured three-dimensional scanner such as a scanner configured to obtain three-dimensional data of a surface geometry of the inside of an outer ear by taking an image of the inside of a human ear other than the inside of the mouth cavity.

Any user of three-dimensional scanner 100, such as an operator including a dentist, a dental nurse, a teacher or a student of a dental college, a dental technician, an engineer of a manufacturer, a worker in a manufacturing factory, and the like, may be applicable so long as the user obtains three-dimensional data of object 99 such as a tooth and a soft tissue with the use of three-dimensional scanner 100. Any subject of scanning by three-dimensional scanner 100, such as a patient at a dentist or a subject in a dental college, may be applicable so long as the subject can be a subject to be scanned by three-dimensional scanner 100.

As shown in FIG. 1, three-dimensional scanner 100 includes a handpiece 70, a control device 40, a display 50, and a power supply 45. Handpiece 70 is a hand-held member, and includes a probe 10, a connection portion 20, and an optical measurement unit 30.

Probe 10 is inserted in the mouth cavity to project light having a pattern (which is simply also referred to as a "pattern" below) onto object 99 such as a tooth and a soft tissue. Probe 10 guides light reflected from object 99 on which the pattern is projected to optical measurement unit 30. Probe 10 is removably attached to connection portion 20 while it covers an outer periphery of a tip end of connection portion 20.

Connection portion 20 is a part of optical measurement unit 30 that protrudes from optical measurement unit 30, and it is in a shape that allows fitting to a root of probe 10. Connection portion 20 includes an optical component such as a lens system for guiding light taken by probe 10 to optical measurement unit 30, a cover glass, an optical filter, and a phase plate (for example, a ¼ wave plate).

Optical measurement unit 30 projects a pattern on object 99 through probe 10 and takes an image of the projected pattern. Optical measurement unit 30 according to the embodiment is configured to obtain a three-dimensional geometry based on principles of the focus method as will be described below.

Control device 40 controls an operation of optical measurement unit 30 and obtains the three-dimensional geometry by processing an image taken by optical measurement unit 30. Control device 40 includes a computing unit 41 and a storage unit 42.

Computing unit 41 is a computing entity (computer) that performs various types of processing by executing various programs. Computing unit 41 is implemented by a processor such as a central processing unit (CPU) or a micro-processing unit (MPU). Though the processor which represents an exemplary computing unit 41 performs functions to perform various types of processing by executing a program, some or all of these functions may be performed by dedicated hardware circuitry such as an application specific integrated circuit (ASIC) or a field-programmable gate array (FPGA). The "processor" is not limited to a processor in a narrow sense that performs processing in accordance with a stored program architecture like the CPU or the MPU, but may encompass hard-wired circuitry such as the ASIC or the FPGA. Therefore, the "processor" representing exemplary computing unit 41 can also be read as processing circuitry, processing by which is defined in advance by a computer readable code and/or hard-wired circuitry. Computing unit 41 may be implemented by a single chip or a plurality of chips. Furthermore, the processor and relating processing circuitry may be implemented by a plurality of computers connected to one another through wires or wirelessly over a local area network or a wireless network. The processor and the relating processing circuitry may be implemented by a cloud computer that performs remote computation based on input data and outputs a result of computation to another device located at a remote position.

Storage unit 42 includes a memory and a storage device which are not shown. The memory includes a volatile storage area (for example, a working area) where a program code or a work memory is temporarily stored in execution of various programs by computing unit 41. Examples of the memory include a volatile memory such as a dynamic random access memory (DRAM) and a static random access memory (SRAM) or a non-volatile memory such as a read only memory (ROM) and a flash memory. Various programs to be executed by computing unit 41 or various types of data are stored in the storage device. The storage device may be implemented by one or more non-transitory computer readable media or one or more computer readable storage media. Examples of the storage device include a hard disk drive (HDD) and a solid state drive (SSD).

In three-dimensional scanner 100 according to the embodiment, a control program 43 to be executed by computing unit 41 is stored in storage unit 42.

Computing unit 41 performs processing involved with amplitude control for controlling reciprocating linear motion of a lens 81 by executing control program 43. Details of amplitude control will be described later.

Control device 40 can also output obtained three-dimensional data to display 50 or receive input of information such as setting of optical measurement unit 30 through a not-shown input device or the like.

Though control device 40 is configured separately from handpiece 70 in three-dimensional scanner 100 according to the embodiment, at least one or all of functions of computing unit 41 and storage unit 42 of control device 40 may be performed by handpiece 70 so long as control device 40 is sufficiently small in size and light in weight to such an extent as being lifted by one hand.

Though each constituent element (30, 40, 45, or 50) of three-dimensional scanner 100 is drawn as being routed through a cable (a bold line in the figure) in the example in FIG. 1, a part or the entirety of such routing may be established by connection by wireless communication.

Display 50 shows a three-dimensional geometry of object 99 represented by three-dimensional data obtained by control device 40. Display 50 can also show other information such as setting information of optical measurement unit 30, patient information, a scanner activation state, an operation manual, and a help screen. For example, a stationary liquid crystal display, a wearable device of a head-mounted type or a glass type, or the like may be applicable as display 50. Three-dimensional scanner 100 may include a plurality of displays 50, and the three-dimensional geometry of object 99 and other information may be shown on the plurality of displays 50 simultaneously or in a split manner.

Power supply 45 supplies electric power to optical measurement unit 30 and control device 40. Though power supply 45 may be provided outside control device 40 as shown in FIG. 1, it may be provided in the inside of control device 40 or the inside of handpiece 70. A plurality of power supplies 45 may be provided to individually feed power to control device 40, optical measurement unit 30, and display 50.

[Configuration of Handpiece]

Figure 2:
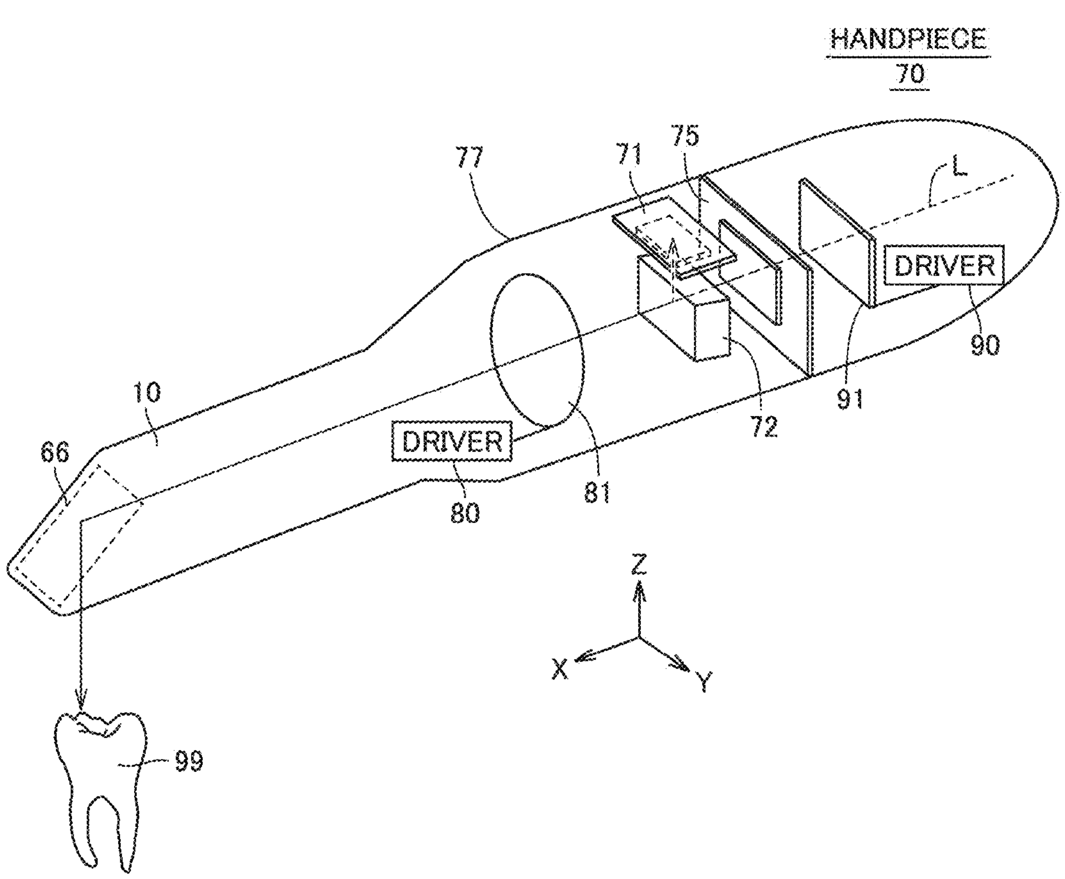
FIG. 2 is a diagram showing a configuration of a handpiece according to the embodiment.
Figure 3:
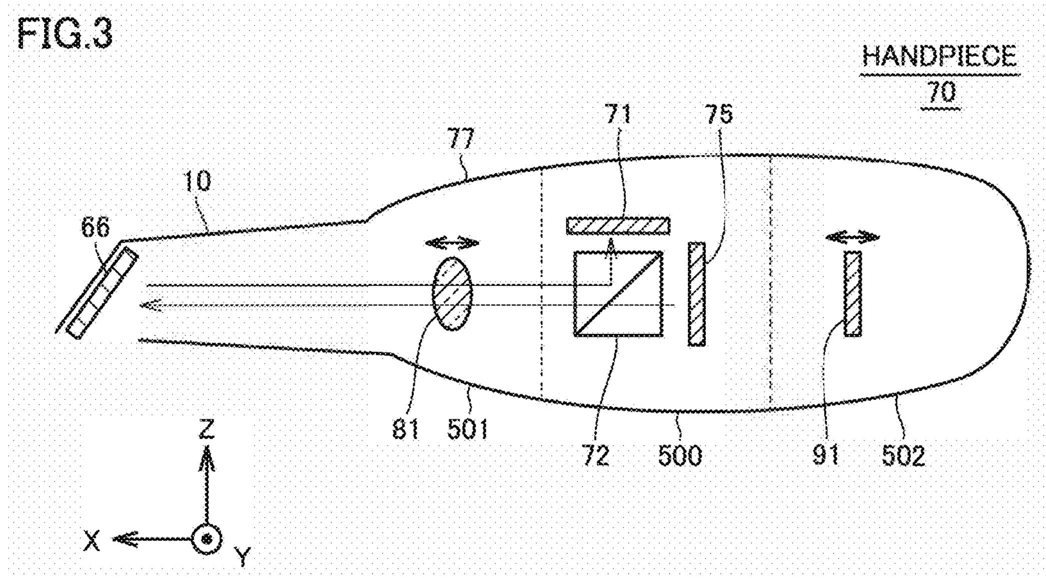
FIG. 3 is a diagram showing an X-Z cross-section of the handpiece according to the embodiment.

FIG. 2 is a diagram showing a configuration of handpiece 70 according to the embodiment. FIG. 3 is a diagram showing an X-Z cross-section of handpiece 70 according to the embodiment. Each member in handpiece 70 shown in FIGS. 2 and 3 is accommodated in optical measurement unit 30 shown in FIG. 1.

As shown in FIGS. 2 and 3, handpiece 70 includes a projection light generator 75, lens 81, an optical sensor 71, and a prism 72 in the inside of a hand-held housing 77. Optical sensor 71 is an exemplary "imaging unit." In addition thereto, handpiece 70 may include a reflector that reflects light toward object 99. In the embodiment, for the sake of convenience of description, a virtual straight line representing a direction of reciprocating linear motion of lens 81 is denoted as L, and an axis in parallel to straight line L is referred to as an X axis, an upward axis perpendicular to straight line L on the sheet plane in FIG. 2 is referred to as a Z axis, and an axis perpendicular to each of the X axis and the Z axis is referred to as a Y axis.

Projection light generator 75 is implemented by a laser element or a light emitting diode (LED) that serves as a light source. Light from projection light generator 75 passes through prism 72 and lens 81 via a projection pattern screen (not shown) that is arranged in front of projection light generator 75 and generates a projection pattern, and is emitted to object 99 through a reflection portion 66 provided in probe 10 and reflected by object 99. Light reflected at object 99 passes again through lens 81 via reflection portion 66 and enters prism 72. Prism 72 changes a direction of travel of light from object 99 to a direction in which optical sensor 71 is located (in this example, a Z-axis direction). Light the direction of travel of which is changed by prism 72 is detected by optical sensor 71. Though light from projection light generator 75 and light reflected at object 99 and guided to prism 72 are shown separately from each other in the example shown in FIG. 3, this representation is for the sake of description for facilitated understanding, and actually, handpiece 70 is configured such that both of them are coaxially guided.

In an example where a three-dimensional geometry is obtained by using the technique of the focus method, light that passes through a pattern generation element (not shown) provided between lens 81 and object 99 is projected on object 99. As lens 81 makes reciprocating linear motion along the same straight line (for example, straight line L as illustrated), a focal position of the projection pattern is varied. Optical sensor 71 takes an image of object 99 present at the focal position of the projection pattern by detecting light from object 99 at a prescribed frame rate each time the focal position of the projection pattern is varied, under the control by control device 40. Control device 40 can change the frame rate by changing a shutter speed of optical sensor 71. Control device 40 obtains three-dimensional data of the surface geometry of object 99 by computing geometrical information of object 99 based on a position of lens 81 and a result of detection by optical sensor 71 at that time.

Lens 81 is driven by a lens driver 80 and makes reciprocating linear motion. When lens 81 makes reciprocating linear motion in a direction shown with straight line L (an X-axis direction), a position of the center of gravity of handpiece 70 moves by a mass of lens 81, which is transmitted as vibration to a user's hand with which handpiece 70 is held. In order to cancel vibration, handpiece 70 further includes a counterweight 91 in the inside of housing 77. Counterweight 91 is driven by a counterweight driver 90 and makes reciprocating linear motion in a direction opposite to reciprocating motion of lens 81.

Counterweight 91 is provided on a rear surface side of projection light generator 75 in the X-axis direction so as not to cut off an optical path between object 99 and lens 81 and an optical path between lens 81 and optical sensor 71.

Specifically, as shown in FIG. 3, handpiece 70 is provided with a first accommodation portion 501 located in a front portion of handpiece 70 and a second accommodation portion 502 located in a rear portion of handpiece 70 in housing 77. Lens 81 is accommodated in first accommodation portion 501 and counterweight 91 is accommodated in second accommodation portion 502. Handpiece 70 is further provided with a coupling accommodation portion 500 between first accommodation portion 501 and second accommodation portion 502, coupling accommodation portion 500 coupling lens 81 held in first accommodation portion 501 and counterweight 91 held in second accommodation portion 502 to each other. Optical sensor 71, prism 72, and projection light generator 75 described above are accommodated in coupling accommodation portion 500.

Figure 4:
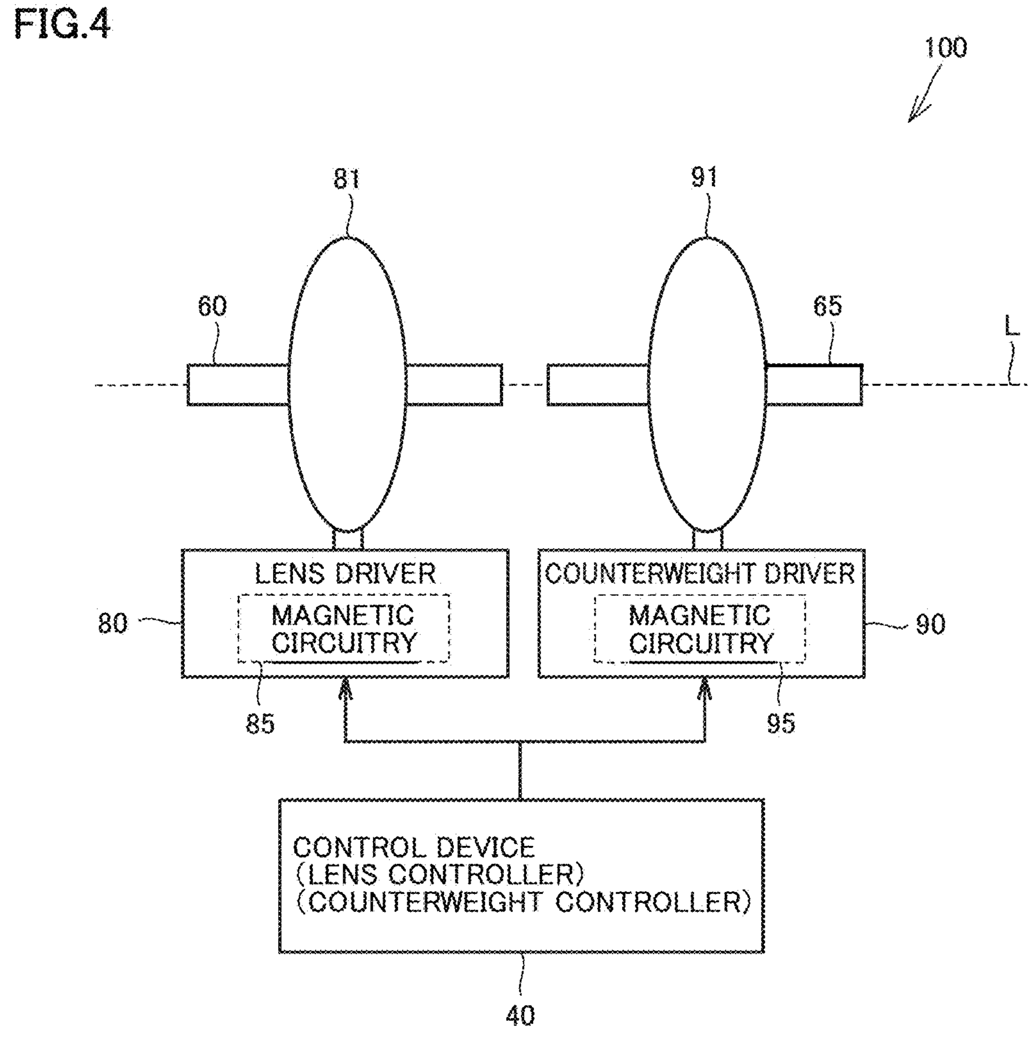
FIG. 4 is a diagram for illustrating positional relation between a lens and a counterweight in the three-dimensional scanner according to the embodiment.

FIG. 4 is a diagram for illustrating positional relation between lens 81 and counterweight 91 in three-dimensional scanner 100 according to the embodiment. An example shown in FIG. 4 does not show housing 77. As shown in FIG. 4, lens 81 is supported by a linear guide 60 in parallel to straight line L to make reciprocating linear motion in the direction of straight line L.

Furthermore, lens driver 80 causes lens 81 held by a mover to make reciprocating linear motion in the direction of straight line L by means of magnetic circuitry 85. In other words, lens driver 80 is implemented by a linear motor.

Counterweight 91 is a weight provided on straight line L in a direction of the linear motion of lens 81, the weight being equal in mass to lens 81. Counterweight 91 is supported by a linear guide 65 in parallel to straight line L to make reciprocating linear motion in the direction of straight line L. Though linear guide 60 and linear guide 65 are different members in the embodiment, linear guide 60 and linear guide 65 may be formed from one continuous member.

Counterweight driver 90 causes counterweight 91 held by a mover to make reciprocating linear motion in the direction of straight line L by means of magnetic circuitry 95. In other words, counterweight driver 90 is implemented by a linear motor.

A specific configuration of lens driver 80 and counterweight driver 90 each implemented by the linear motor will be described later. Lens driver 80 and counterweight driver 90 are also simply collectively referred to as a "linear motor" below. Each of lens driver 80 and counterweight driver 90 is controlled by control device 40. Control device 40 is an exemplary "lens controller" and an exemplary "counterweight controller." Though lens driver 80 and counterweight driver 90 are controlled by control device 40 in common in the embodiment, lens driver 80 and counterweight driver 90 may be controlled by control devices different from each other.

When lens driver 80 causes lens 81 to make reciprocating linear motion in the direction of straight line L which defines an optical axis, counterweight driver 90 causes counterweight 91 to make reciprocating linear motion in a direction opposite to reciprocating motion of lens 81 by a distance as long as the distance of reciprocating linear motion of lens 81. For example, when lens 81 moves along straight line L by 10 mm in a direction toward object 99, counterweight 91 moves along straight line L by 10 mm in a direction away from object 99. When lens 81 moves along straight line L by 15 mm in the direction away from object 99, counterweight 91 moves along straight line L by 15 mm in the direction toward object 99.

As counterweight 91 thus makes reciprocating linear motion in the direction opposite to reciprocating motion of lens 81 by the distance as long as the distance of reciprocating linear motion of lens 81, imbalance in center of gravity of handpiece 70 due to reciprocating linear motion of lens 81 can be canceled. Counterweight 91 can thus cancel vibration caused by reciprocating linear motion of lens 81.

[Configuration of Linear Motor]

Figure 5:
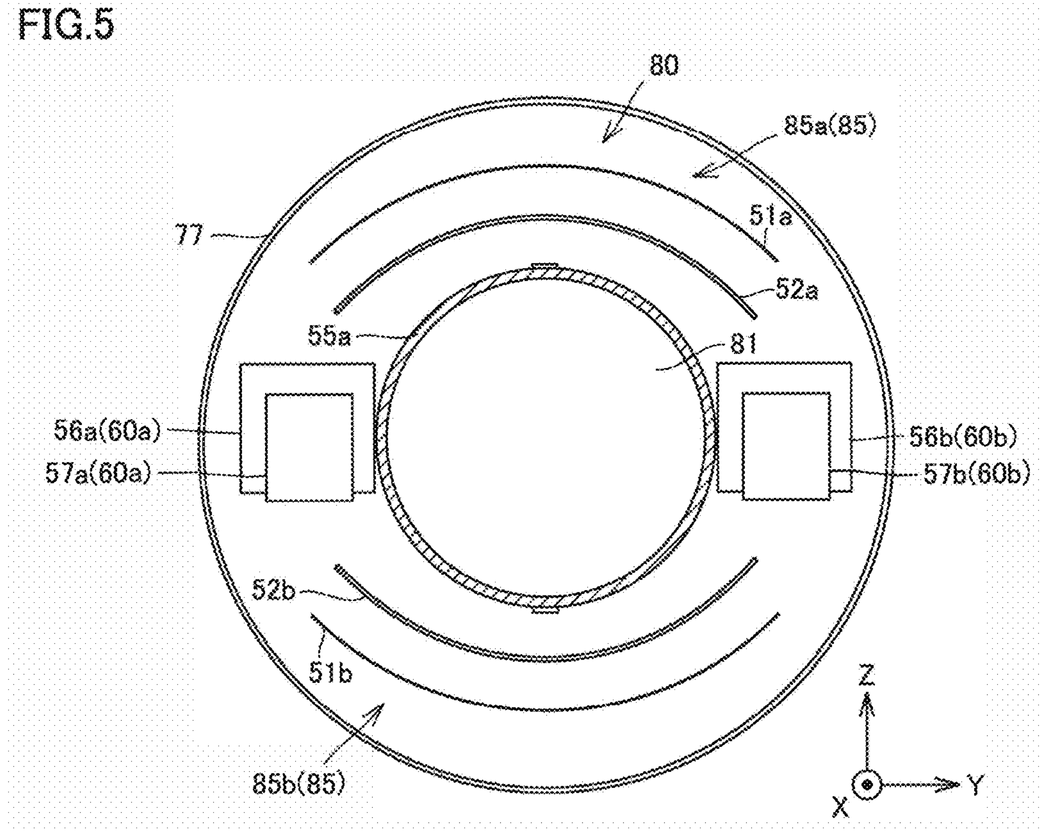
FIG. 5 is a diagram showing a Y-Z cross-section of a linear motor according to the embodiment.
Figure 6:
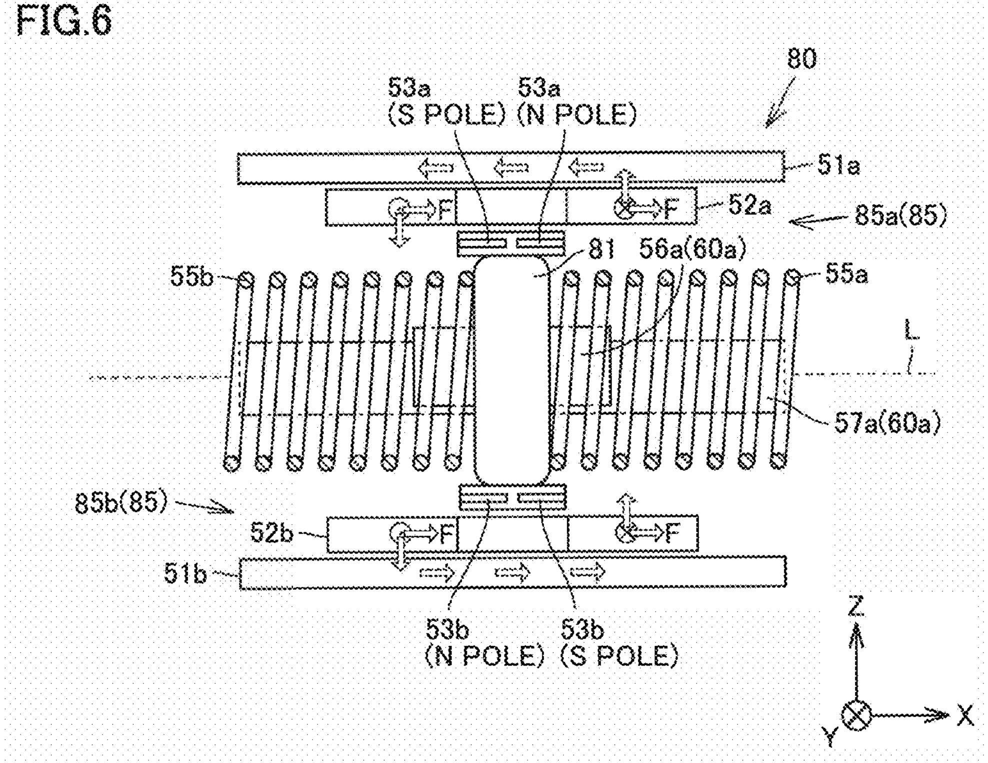
FIG. 6 is a diagram showing an X-Z cross-section of the linear motor according to the embodiment.

FIG. 5 is a diagram showing a Y-Z cross-section of the linear motor according to the embodiment. FIG. 6 is a diagram showing an X-Z cross-section of the linear motor according to the embodiment. In the example shown in FIGS. 5 and 6, of the linear motors, the configuration of lens driver 80 will be described. Counterweight driver 90 is also similar in configuration to lens driver 80. Specifically, in the case of counterweight driver 90, in the example shown in FIGS. 5 and 6, lens 81 is replaced with counterweight 91 but the counterweight driver is otherwise similar in configuration to lens driver 80.

As shown in FIGS. 5 and 6, in lens driver 80, in order to provide lens 81 substantially in a circular shape in a central portion, members for allowing lens 81 to make reciprocating linear motion are arranged around lens 81, and lens driver 80 is in an elongated hollow shape along straight line L which represents the direction of linear motion. Since the configuration is such that substantially circular lens 81 is provided in the central portion of lens driver 80, light can pass through the central portion of lens driver 80.

Specifically, as shown in FIG. 5, in lens driver 80, a linear guide **60*a* composed of a rail 57*a* and a block 56*a* and a linear guide 60*b* composed of a rail 57*b* and a block 56*b* are provided in an outer circumferential portion of lens 81. A plurality of linear guides 60*a* and 60*b* are thus arranged at positions different from each other on an outer circumferential side of lens 81**.

More specifically, the plurality of linear guides **60*a* and 60*b* are arranged in parallel to each other at positions in rotation symmetry, with the optical axis (straight line L) that is in parallel to the direction of linear motion of lens 81 and passes through the center of lens 81 being defined as a rotation axis. For example, when each of the plurality of linear guides 60*a* and 60*b* is turned by 180 degrees with straight line L being defined as the rotation axis in FIG. 5, linear guide 60*a* is arranged at the position of linear guide 60*b* and linear guide 60*b* is arranged at the position of linear guide 60*a*. Though not shown, a plurality of linear guides 65 are arranged also at similar positions. In other words, the plurality of linear guides 65 are arranged in parallel to each other at positions in rotation symmetry with an axis (straight line L) that is in parallel to the direction of linear motion of counterweight 91 and passes through the center of counterweight 91** being defined as a rotation axis.

Block **56*a* of linear guide 60*a* supports lens 81 and is fitted to rail 57*a*, and causes lens 81 to make reciprocating linear motion by moving in the linear direction along rail 57*a*. Block 56*b* of linear guide 60*b* supports lens 81 at a position different from block 56*a* and is fitted to rail 57*b*, and causes lens 81 to make reciprocating linear motion by moving in the linear direction along rail 57*b*. Linear guides 60*a* and 60*b* correspond to linear guide 60 described with reference to FIG. 4**.

Furthermore, as shown in FIG. 6, a spring **55*a* and a spring 55*b* as elastic members are provided along an outer circumference of lens 81 to surround the outer circumference of lens 81 but not to cut off an optical path in the central portion of lens 81. A coil spring or the like is applied as spring 55*a* and spring 55*b***. Without being limited to the spring, any member such as rubber may be applicable as the elastic member so long as the member deforms when force is applied thereto whereas it returns to the original state when force is removed.

Spring **55*a* and spring 55*b* have one ends abutting on lens 81 and the other ends fixed in housing 77. Furthermore, spring 55*a* and spring 55*b* are held in housing 77 such that deformation thereof in an X direction is permitted and they are less likely to deform in a Y-Z direction. Spring 55*a* and spring 55*b* thus arranged apply elastic force to lens 81 in the direction of linear motion. Spring 55*a* and spring 55*b* may substantially be equal in diameter to lens 81 so as to be able to fix lens 81** by sandwiching the same therebetween.

On an outer side (a side away from the center of lens 81 in a Z direction) of spring **55*a* and spring 55*b*, magnetic circuitry 85*a* for reciprocating linear motion of lens 81 in the direction of straight line L is provided. Magnetic circuitry 85*a* includes a magnet 53*a* composed of the N pole and the S pole and a coil 52*a* arranged on the outer side (the side away from the center of lens 81 in the Z direction) of magnet 53*a***.

Magnet **53*a* is a mover that can be moved in the direction of straight line L. As magnet 53*a* makes reciprocating linear motion in the X direction along straight line L, lens 81 can also make reciprocating linear motion in the X direction along straight line L. Coil 52*a*** is a stator.

A yoke **51*a* is provided on the further outer side (the side away from the center of lens 81 in the Z direction) of coil 52*a*. Yoke 51*a* is a stator similarly to coil 52*a*. On a side opposite to magnetic circuitry 85*a* with lens 81 being interposed, magnetic circuitry 85*b* for reciprocating linear motion of lens 81 in the direction of straight line L is provided. Magnetic circuitry 85*b* includes a magnet 53*b* composed of the N pole and the S pole and a coil 52*b* arranged on the outer side (the side away from the center of lens 81 in the Z direction) of magnet 53*b***.

Magnet **53*b* is a mover that can be moved in the direction of straight line L. As magnet 53*b* makes reciprocating linear motion in the X direction along straight line L, lens 81 can also make reciprocating linear motion in the X direction along straight line L. Coil 52***b* is a stator.

A yoke 51*b* is provided on the further outer side of coil 52*b*. Yoke 51*b* is a stator similarly to coil 52*b*. Furthermore, yoke 51*a* and yoke 51*b* which are stators are fixed as appropriate to housing 77 of handpiece 70.

In lens driver 80 configured as such, as magnetic circuitry 85*a* and magnetic circuitry 85*b* apply force to lens 81 in the direction of straight line L, lens 81 makes reciprocating linear motion.

For example, when magnet 53*a* and magnet 53*b* each composed of the N pole and the S pole are arranged in positional relation as shown in FIG. 6 in magnetic circuitry 85*a* and magnetic circuitry 85*b*, magnetic field in a direction as shown with a dotted arrow is produced. In this case, when a drive current (a current in a direction from the front toward the rear on the sheet plane along the Y axis being expressed with "x" and a current in a direction from the rear toward the front on the sheet plane along the Y axis being expressed with ".") as shown in FIG. 6 is fed to coil 52*a* and coil 52*b*, electromagnetic force (F) is produced in the X-axis direction as shown with a solid arrow in accordance with the Fleming's left-hand rule. As electromagnetic force (F) thus produced is applied to magnet 53*a* and magnet 53*b* which are the movers, magnet 53*a* and magnet 53*b* are moved in a direction opposite to electromagnetic force (F). Components relating to motion of an object in an apparatus, such as springs 55*a* and 55*b*, magnets 53*a* and 53*b*, lens 81, coils 52*a* and 52*b*, and a damper containing a viscous lubricant such as grease, are also referred to as a "kinetic system" below.

Lens 81 vibrates in the direction of straight line L as a result of response by the kinetic system, such as inertial force of lens 81, electromagnetic force (F), elastic force of springs 55*a* and 55*b*, and viscous force of the damper. Using this vibration, control device 40 causes lens 81 to make reciprocating linear motion in the direction of straight line L. In other words, control device 40 controls lens driver 80 in constant cycles in accordance with a natural frequency of the kinetic system to feed the drive current to magnetic circuitry 85*a* and magnetic circuitry 85*b*, so that lens 81 can make reciprocating linear motion in the direction of straight line L based on a phenomenon of resonance by the kinetic system. Since the drive current is in proportion to an amount of displacement in reciprocating linear motion of lens 81, control device 40 can vary the amount of displacement in reciprocating linear motion of lens 81 by varying the drive current. For example, as control device 40 increases the drive current, the amount of displacement in reciprocating linear motion of lens 81 can increase, and as control device 40 decreases the drive current, the amount of displacement in reciprocating linear motion of lens 81 can decrease.

As the drive current is thus fed to coil 52*a* and coil 52*b* in accordance with the natural frequency of the kinetic system, lens driver 80 can function as a resonant drive motor that drives lens 81 to move back and forth in the direction of straight line L. In an example where lens 81 is caused to make reciprocating linear motion by a mechanical arrangement in which a mechanical component such as a cam is connected to a motor, the motor should constantly be kept driven while lens 81 is moved. By using the phenomenon of resonance of the kinetic system as in the embodiment, on the other hand, lens 81 can be caused to make reciprocating linear motion simply by feed of the drive current in magnetic circuitry 85*a* and magnetic circuitry 85*b* in constant cycles. Therefore, use of magnetic circuitry 85 as in the embodiment can achieve suppression of power consumption and efficiency. Furthermore, in the case of a cam mechanism, contact noise may be generated by the cam mechanism, or powders resulting from contact may be produced from a cam surface due to deterioration of a cam mechanism portion. By using the phenomenon of resonance of the kinetic system as in the embodiment, such a disadvantage can also be overcome.

As described previously, when lens driver 80 causes lens 81 to make reciprocating linear motion in the direction of straight line L, counterweight driver 90 causes counterweight 91 to make reciprocating linear motion in the direction opposite to reciprocating motion of lens 81 by the distance the same as the distance of motion of lens 81. Lens 81 makes reciprocating linear motion along straight line L, whereas counterweight 91 makes reciprocating linear motion along straight line L in the direction opposite to reciprocating motion of the direction of linear motion of lens 81 in order to cancel imbalance of the center of gravity. The user thus does not feel vibration even when the user uses handpiece 70 by holding the same in his/her hand.

COMPARATIVE EXAMPLE

As described above, three-dimensional scanner 100 is configured to vary a focal position of light that passes through lens 81 by causing lens 81 contained in handpiece 70 to make reciprocating linear motion and to take an image of object 99 present at the focal position of light. The focal position of light that passes through lens 81 is dependent on a range of movement of lens 81 that makes reciprocating linear motion.

In three-dimensional scanner 100, depending on an amplitude of reciprocating motion of lens 81, a depth of field which is a range of a focal position of light that passes through lens 81 may not be stable.

Figure 7:
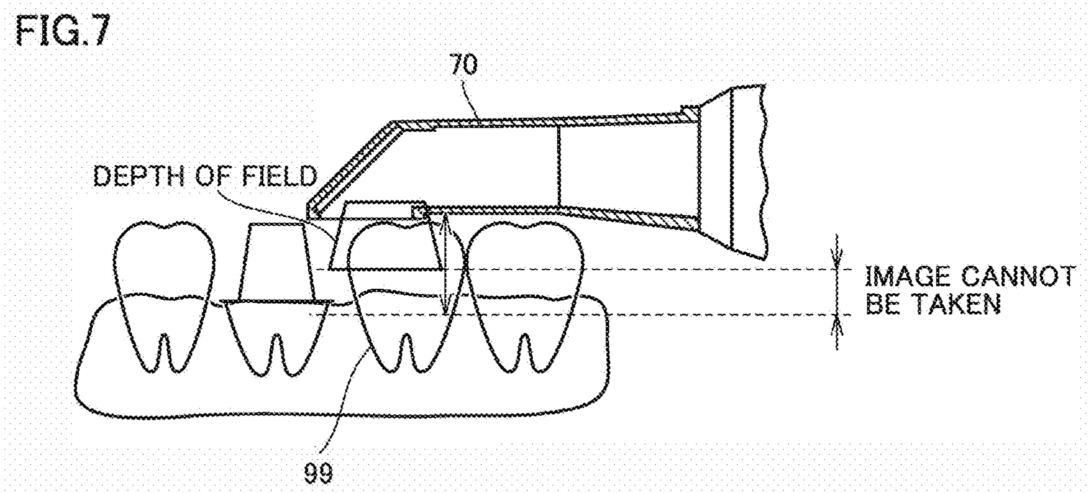
FIG. 7 is a diagram showing an example in which a depth of field is smaller than an appropriate value in the three-dimensional scanner according to a comparative example.

For example, FIG. 7 is a diagram showing an example in which the depth of field is smaller than an appropriate value in the three-dimensional scanner according to a comparative example. When the depth of field is smaller than the appropriate value as shown in FIG. 7, the range that can be imaged in one imaging is excessively narrow, and hence a part of object 99 which is a target of imaging may not be included in the depth of field. For example, in the case of this example, a lower portion of a tooth and a gingiva are not included in the depth of field. Therefore, imaging by the user is difficult and also a time period for imaging increases. Since an image of object 99 cannot be taken in one scanning, the user has to put together imaged portions.

Therefore, since the number of times of operation to put together imaged portions increases, accuracy of obtained three-dimensional data is lowered.

Figure 8:
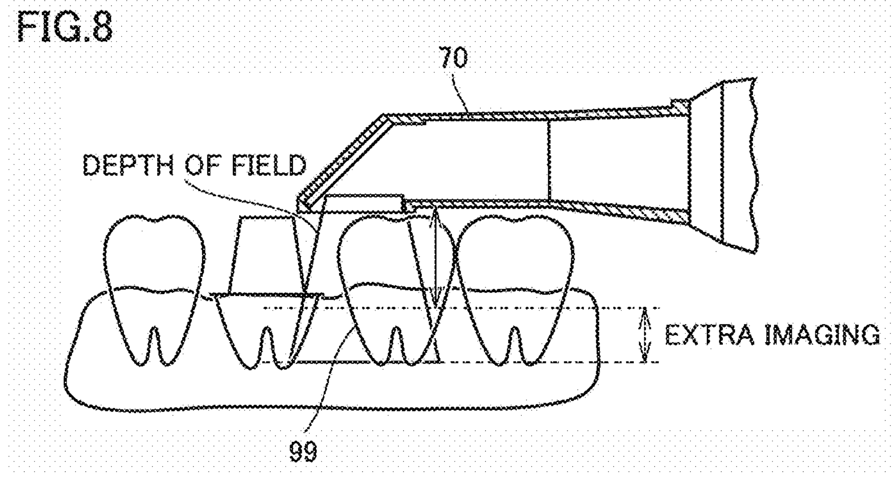
FIG. 8 is a diagram showing an example in which the depth of field is larger than the appropriate value in the three-dimensional scanner according to the comparative example.

FIG. 8 is a diagram showing an example in which the depth of field is larger than the appropriate value in the three-dimensional scanner according to the comparative example. When the depth of field is larger than the appropriate value as shown in FIG. 8, the range that can be imaged in one imaging is excessively large, which may result in imaging of an unnecessary portion (for example, lips, the tongue, or an extra gingival portion) which is not a target of imaging. The user thus has to erase the unnecessary portion. Therefore, computing load for erasure of the unnecessary portion is imposed, and accordingly a computing speed is lowered and an amount of heat generation also increases. A frame rate of optical sensor 71 may be lowered in order to suppress the amount of heat generation. Lowering in frame rate, however, lowers accuracy of obtained three-dimensional data.

Thus, unless the user sets the depth of field to the appropriate value in accordance with object 99 which is the target of imaging, the user is unable to appropriately obtain three-dimensional data of the surface geometry of object 99. Object 99 which is the target of imaging, however, is different depending on a state of the inside of the mouth cavity of a patient and a part which is a target of imaging. Therefore, the user is unable to set the depth of field to a predetermined value. Manual setting of the depth of field to the appropriate value in accordance with object 99 which is the target of imaging requires high skills, and is bothersome for the user. As described below, three-dimensional scanner 100 according to the embodiment is configured to automatically set the depth of field to the appropriate value by changing the amplitude of reciprocating motion of lens 81 in accordance with object 99 which is the target of imaging.

[Control of Operation of Lens in Accordance with Object which is Target of Imaging]

Figure 9:
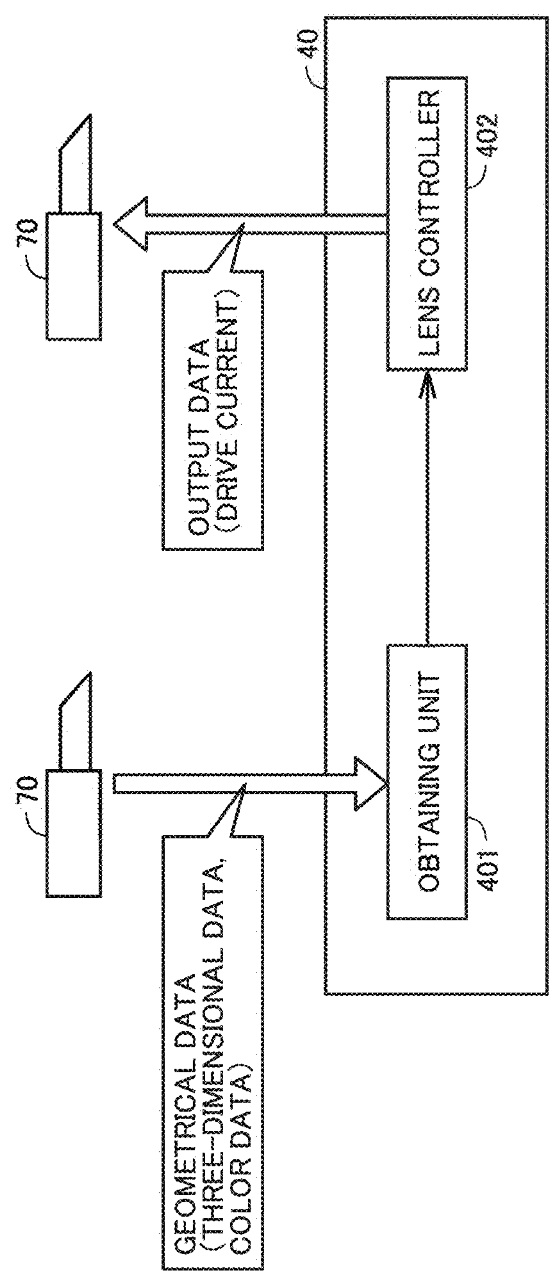
FIG. 9 is a diagram for illustrating a functional configuration of a control device included in the three-dimensional scanner according to the embodiment.

Control of lens 81 in accordance with object 99 which is the target of imaging will be described with reference to FIGS. 9 to 11. FIG. 9 is a diagram for illustrating a functional configuration of control device 40 included in three-dimensional scanner 100 according to the embodiment. As shown in FIG. 9, control device 40 includes an obtaining unit 401 and a lens controller 402 as its main functional configuration. Obtaining unit 401 and lens controller 402 may be included in a functional configuration of computing unit 41, or may be a functional configuration different from computing unit 41.

Obtaining unit 401 obtains geometrical data representing the surface geometry of object 99 based on an image of object 99 taken by optical sensor 71 of handpiece 70. In three-dimensional scanner 100 according to the embodiment, the geometrical data includes three-dimensional data including positional information of each point in a group of points representing the surface geometry of object 99 and color data indicating a color of each point in the group of points (a plurality of points) representing the surface geometry of object 99.

Lens controller 402 controls lens driver 80 by outputting output data indicating the drive current to lens driver 80 in handpiece 70 to carry out amplitude control for changing the amplitude of reciprocating motion of lens 81 based on the geometrical data obtained by obtaining unit 401.

Specifically, lens controller 402 recognizes a position of each point in the group of points representing the surface geometry of object 99 based on the three-dimensional data included in the geometrical data. Furthermore, lens controller 402 recognizes a color of each point in the group of points representing the surface geometry of object 99 based on the color data included in the geometrical data. Lens controller 402 can thus recognize whether each point in the group of points representing the surface geometry of object 99 is a point corresponding to a tooth or a point corresponding to a gingiva. For example, lens controller 402 can recognize that a point the color data of which belongs to a white color type is a point corresponding to the tooth and that a point the color data of which belongs to a red color type (for example, pink) is a point corresponding to the gingiva.

Furthermore, lens controller 402 calculates a ratio of the tooth and a ratio of the gingiva in object 99 included in the current depth of field. Lens controller 402 changes the amplitude of reciprocating motion of lens 81 based on a result of calculation by varying the drive current to be supplied to magnetic circuitry 85 such that the ratio of the tooth included in the depth of field is set to a prescribed value. For example, lens controller 402 changes the amplitude of reciprocating motion of lens 81 by varying the drive current to be supplied to magnetic circuitry 85 such that the ratio of the tooth included in the depth of field is approximately 80% of object 99 included in the depth of field and the ratio of the gingiva included in the depth of field is approximately 20% of object 99 included in the depth of field. Alternatively, lens controller 402 changes the amplitude of reciprocating motion of lens 81 based on the result of calculation by varying the drive current to be supplied to magnetic circuitry 85 such that the ratio of the tooth included in the depth of field is within a prescribed range. For example, lens controller 402 changes the amplitude of reciprocating motion of lens 81 by varying the drive current to be supplied to magnetic circuitry 85 such that the ratio of the tooth included in the depth of field is set to approximately 70% to approximately 90% of object 99 included in the depth of field and the ratio of the gingiva included in the depth of field is set to approximately 10% to approximately 30% of object 99 included in the depth of field. The ratio of the tooth to be included in the depth of field may be determined and set in advance by the user.

Figure 10:
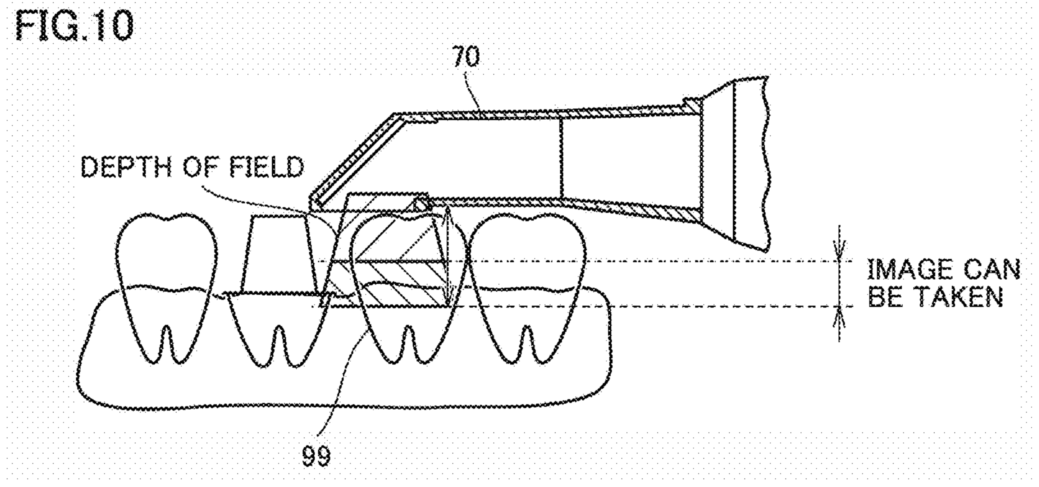
FIGS. 10 and 11 are each a diagram showing exemplary adjustment of the depth of field to an appropriate value in the three-dimensional scanner according to the embodiment.
Figure 11:
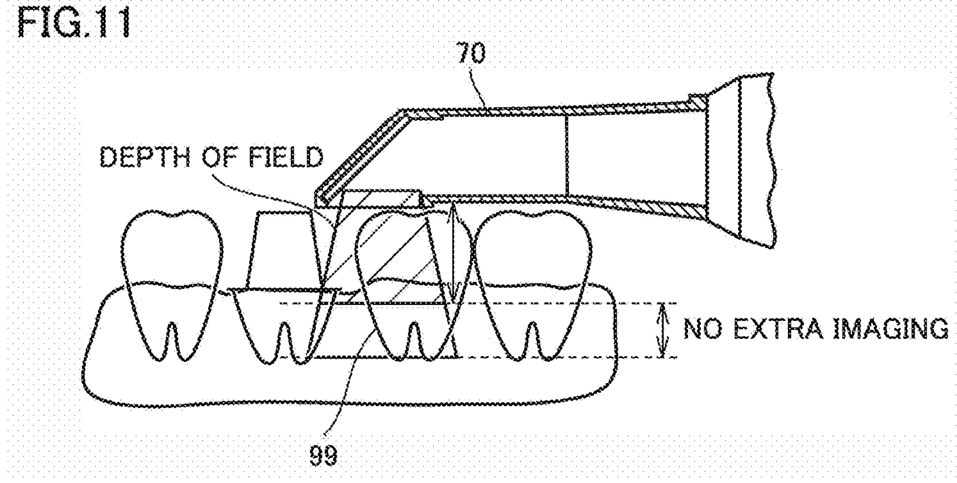

FIGS. 10 and 11 are each a diagram showing exemplary adjustment of the depth of field to the appropriate value in three-dimensional scanner 100 according to the embodiment. FIG. 10 shows exemplary adjustment of the depth of field to the appropriate value from a value smaller than the appropriate value as in the comparative example shown in FIG. 7. Since the range that can be imaged in one imaging is excessively narrow in the comparative example in FIG. 7, a part (for example, the lower portion of the tooth and the gingiva) of object 99 which is the target of imaging is not included in the depth of field. When the depth of field is adjusted to the appropriate value as shown in FIG. 10, however, the range that can be imaged in one imaging is set to an appropriate range. Since the amplitude of reciprocating motion of lens 81 increases as a result of increase in drive current by lens controller 402 in this example, the depth of field is made larger. Consequently, the part (for example, the lower portion of the tooth and the gingiva) of object 99 which is the target of imaging is included in the depth of field. For example, the ratio of the tooth in object 99 included in the depth of field is approximately 80% (or approximately 70% to approximately 90%) and the ratio of the gingiva is approximately 20% (or approximately 10% to approximately 30%), and hence the user can appropriately obtain the three-dimensional data of the surface geometry of object 99 by one scanning.

FIG. 11 shows exemplary adjustment of the depth of field to the appropriate value from a value larger than the appropriate value as in the comparative example shown in FIG. 8. Since the range that can be imaged in one imaging is excessively large in the comparative example in FIG. 8, the image of the unnecessary portion (for example, the lips, the tongue, or the extra gingival portion) which is not the target of imaging may be taken. When the depth of field is adjusted to the appropriate value as shown in FIG. 11, however, the range that can be imaged in one imaging is set to an appropriate range. Since the amplitude of reciprocating motion of lens 81 is made smaller as a result of decrease in drive current by lens controller 402 in this example, the depth of field is made smaller. Consequently, the unnecessary portion (for example, the lips, the tongue, or the extra gingival portion) which is not the target of imaging is not included in the depth of field. For example, the ratio of the tooth in object 99 included in the depth of field is approximately 80% (or approximately 70% to approximately 90%)

and the ratio of the gingiva is approximately 20% (or approximately 10% to approximately 30%), and hence the user can appropriately obtain the three-dimensional data of the surface geometry of object 99 by one scanning.

[Control of Frame Rate]

As described above, control device 40 varies the amount of displacement in reciprocating linear motion of lens 81 by carrying out amplitude control based on the obtained geometrical data. With increase in amount of displacement of lens 81, a range of imaging by optical sensor 71 becomes wider. Then, in order to ensure accuracy in measurement after amplitude control as high as that before amplitude control, control device 40 controls optical sensor 71 such that a frame rate thereof is higher than before amplitude control. Decrease in amount of displacement of lens 81, on the other hand, narrows the range of imaging by optical sensor 71. Then, in order to ensure accuracy in measurement after amplitude control as high as that before amplitude control, control device 40 controls optical sensor 71 such that a frame rate thereof is lower than before amplitude control.

Since three-dimensional scanner 100 can thus take an image of object 99 at a resolution as high as that before amplitude control even when the depth of field is varied by changing the amplitude of lens 81 in amplitude control, accuracy in measurement as high as that before amplitude control can be ensured.

[Process Flow in Control Device]

Figure 12:
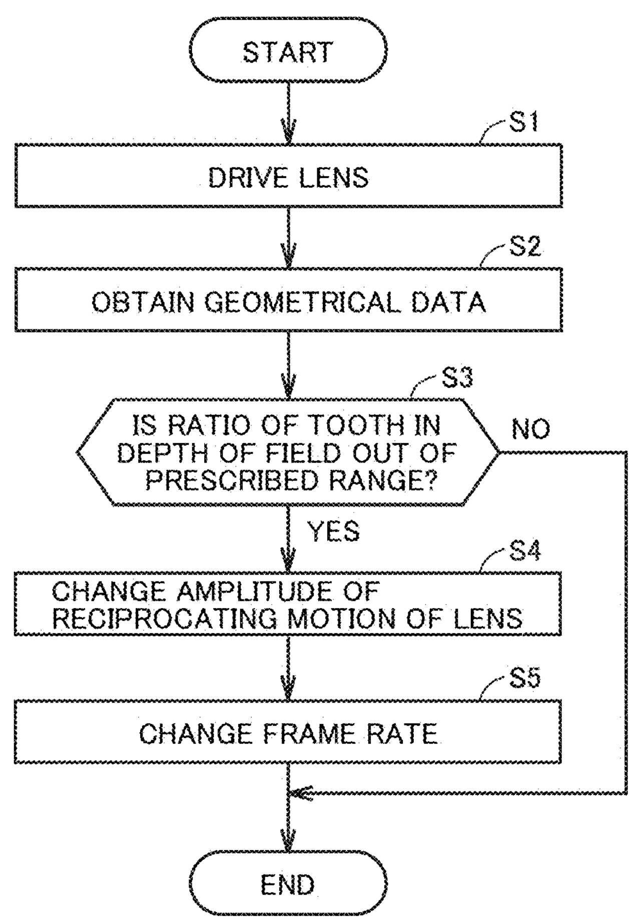
FIG. 12 is a flowchart of amplitude control carried out by a control device in the three-dimensional scanner according to the embodiment.

FIG. 12 is a flowchart of amplitude control carried out by control device 40 in three-dimensional scanner 100 according to the embodiment. Each STEP (which is denoted as "S" below) shown in FIG. 12 is performed by execution of control program 43 by computing unit 41 of control device 40.

As shown in FIG. 12, control device 40 has the drive current supplied to magnetic circuitry 85 to drive lens 81 to make reciprocating linear motion (S1). Control device 40 obtains geometrical data representing the surface geometry of object 99 based on an image of object 99 taken by optical sensor 71 (S2).

Control device 40 determines whether or not the ratio of the tooth in object 99 included in the current depth of field is at a prescribed value (or within a prescribed range) based on the geometrical data (S3). For example, control device 40 determines based on the geometrical data, whether or not the ratio of the tooth in object 99 included in the current depth of field is approximately 80% (or within a range from approximately 70% to approximately 90%). When the ratio of the tooth in object 99 included in the current depth of field is at the prescribed value (or within the prescribed range) (NO in S3), control device 40 quits the present process flow because the current depth of field has been set to the appropriate value.

When the ratio of the tooth in object 99 included in the current depth of field is not at the prescribed value (or not within the prescribed range) (YES in S3), control device 40 changes the amplitude of reciprocating motion of lens 81 by varying the drive current to be supplied to magnetic circuitry 85 such that the ratio of the tooth included in the depth of field is set to the prescribed value (for example, approximately 80%) or within the prescribed range (for example, approximately 70% to approximately 90%) (S4).

When control device 40 changes the amplitude of lens 81 in reciprocating linear motion, it controls optical sensor 71 to change the frame rate (S5). Thereafter, the control device quits the present process flow.

As set forth above, three-dimensional scanner 100 according to the embodiment can set the depth of field to the appropriate value in obtaining the three-dimensional data of the surface geometry of object 99 by changing the amplitude of reciprocating motion of lens 81 based on the geometrical data representing the surface geometry obtained based on the image taken by optical sensor 71. Since the ratio of the tooth in object 99 included in the depth of field is approximately 80% (or approximately 70% to approximately 90%) and the ratio of the gingiva is approximately 20% (or approximately 10% to approximately 30%), the user can appropriately obtain the three-dimensional data of the surface geometry of object 99 by one scanning.

<Modification>

The present disclosure is not limited to the embodiment above, but can variously be modified and applied. A modification applicable to the present disclosure will be described below. Only a difference of three-dimensional scanner 100 according to the modification from three-dimensional scanner 100 according to the embodiment will be described, and a component identical to that of three-dimensional scanner 100 according to the embodiment has the same reference character allotted and description thereof will not be repeated.

In three-dimensional scanner 100 according to the embodiment, control device 40 is configured to recognize whether each point in the group of points representing the surface geometry of object 99 is the point corresponding to the tooth or the point corresponding to the gingiva based on the three-dimensional data and the color data included in the geometrical data and to change the amplitude of reciprocating motion of the lens based on a result of recognition. In three-dimensional scanner 100 according to the modification, control device 40 may be configured to change the amplitude of reciprocating motion of the lens with the use of artificial intelligence (AI).

Figure 13:
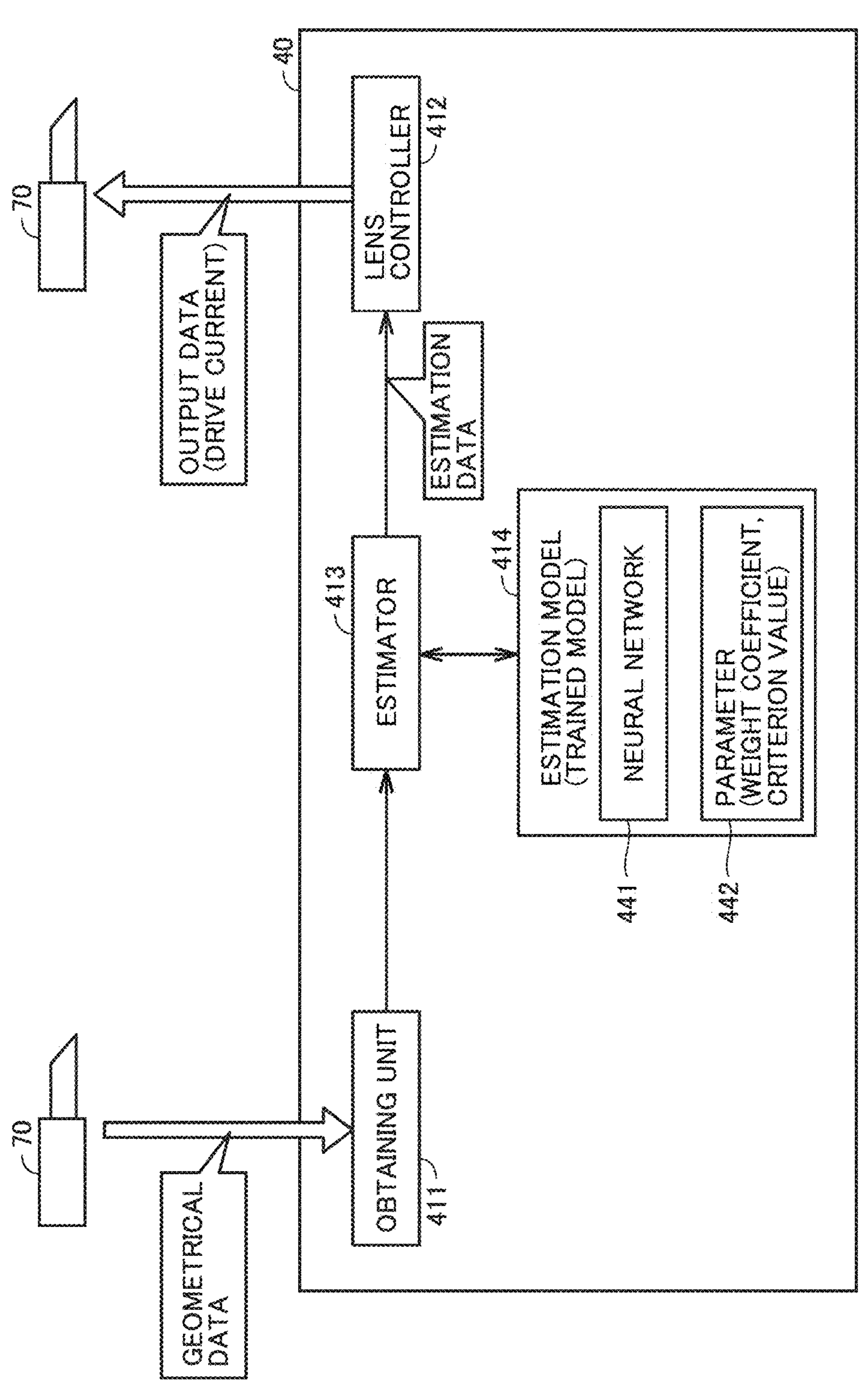
FIG. 13 is a diagram for illustrating a functional configuration of the control device included in the three-dimensional scanner according to a modification.

FIG. 13 is a diagram for illustrating a functional configuration of control device 40 included in three-dimensional scanner 100 according to the modification. As shown in FIG. 13, control device 40 includes, as its main functional configuration, an obtaining unit 411, a lens controller 412, an estimator 413, and an estimation model 414. Obtaining unit 411, lens controller 412, and estimator 413 may be included in a functional configuration of computing unit 41 or may be a functional configuration different from computing unit 41. Estimation model 414 may be stored in storage unit 42.

Obtaining unit 411 obtains the geometrical data representing the surface geometry of object 99 based on the image of object 99 taken by optical sensor 71 of handpiece 70. Estimator 413 generates estimation data based on the geometrical data obtained by obtaining unit 411 and estimation model 414 (a trained model). Lens controller 412 controls lens driver 80 by outputting output data indicating the drive current to lens driver 80 in handpiece 70 based on the estimation data generated by estimator 413, so as to carry out amplitude control for changing the amplitude of reciprocating motion of lens 81 based on the geometrical data obtained by obtaining unit 401.

Estimation model 414 includes a neural network 441 and a parameter 442 to be used by neural network 441. Parameter 442 includes a weight coefficient, a criterion value, and the like to be used for calculation by neural network 441.

FIG. 14 is a diagram for explaining the geometrical data, the estimation data, and the output data in three-dimensional scanner 100 according to the modification. As shown in FIG. 14, in three-dimensional scanner 100 according to the modification, a plurality of patterns such as patterns A to L are assumed depending on contents in the geometrical data, the estimation data, and the output data.

[Pattern A]

In pattern A, the geometrical data includes two-dimensional data, the estimation data includes data indicating the ratio of the tooth in object 99 included in the current depth of field, and the output data includes the drive current to be supplied to magnetic circuitry 85. The two-dimensional data included in the geometrical data is generated based on three-dimensional data obtained by scanning by handpiece 70 and corresponds to a two-dimensional image in which object 99 which is the target of imaging is viewed from any point of view. For example, control device 40 can generate the two-dimensional image showing two-dimensional object 99 viewed from any point of view by processing or editing the three-dimensional data including positional information (the coordinate along axes in the vertical direction, the lateral direction, and the height direction) of each point in the group of points representing the surface geometry of object 99, and obtain the two-dimensional data including positional information (the vertical direction and the lateral direction) of each point in the group of points representing the surface geometry of object 99 shown in the two-dimensional image.

In a training phase, estimation model 414 is trained (machine trained) to estimate the estimation data based on the geometrical data, with the use of training data including the two-dimensional data included in the geometrical data and ground truth data indicating the ratio of the tooth in object 99 included in the depth of field.

Specifically, in the training phase, when estimation model 414 receives input of the two-dimensional data of imaged object 99, it extracts, with the use of neural network 441, a feature of the surface geometry of object 99 based on the two-dimensional data, and estimates the ratio of the tooth in object 99 included in the depth of field based on the extracted feature. Estimation model 414 compares the estimated ratio of the tooth with the ratio of the tooth included in the ground truth data. When the ratios are equal to each other, the estimation model does not update parameter 442, whereas when the ratios are not equal to each other, the estimation model updates parameter 442 such that they are equal to each other to optimize parameter 442. Estimation model 414 is thus machine trained by optimization of parameter 442 based on the training data including the two-dimensional data which is input data and the ratio of the tooth in object 99 included in the depth of field, which is the ground truth data. Estimation model 414 can thus generate the estimation data indicating the ratio of the tooth in object 99 included in the depth of field based on the two-dimensional data of imaged object 99.

In a practical use phase, when estimator 413 of control device 40 obtains as the geometrical data, the two-dimensional data generated based on the three-dimensional data obtained by scanning by handpiece 70, it generates the estimation data indicating the ratio of the tooth in object 99 included in the depth of field based on the obtained two-dimensional data. Lens controller 412 of control device 40 determines based on the estimation data generated by estimator 413, a value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate the ratio of the tooth included in the depth of field based on the two-dimensional data of the surface geometry of object 99 imaged by handpiece 70, and set the depth of field to the appropriate value by changing the amplitude of reciprocating motion of lens 81 based on the result of estimation.

[Pattern B]

In pattern B, the geometrical data includes the two-dimensional data, the estimation data includes data indicating a result of identification of object 99 included in the current depth of field, and the output data includes the drive current to be supplied to magnetic circuitry 85.

In the training phase, estimation model 414 is trained (machine trained) to estimate the estimation data based on the geometrical data, with the use of training data including the two-dimensional data included in the geometrical data and ground truth data indicating the result of identification of object 99 included in the depth of field.

Specifically, in the training phase, when estimation model 414 receives input of the two-dimensional data of imaged object 99, it extracts, with the use of neural network 441, a feature of the surface geometry of object 99 based on the two-dimensional data, and identifies object 99 included in the depth of field based on the extracted feature. For example, estimation model 414 specifies a portion of the tooth and a portion of the gingiva in object 99 included in the depth of field based on the two-dimensional data. Estimation model 414 compares the result of identification of object 99 with the result of identification of object 99 included in the ground truth data. When the results are equal to each other, the estimation model does not update parameter 442, whereas when the results are not equal to each other, the estimation model updates parameter 442 such that they are equal to each other to optimize parameter 442. Estimation model 414 is thus machine trained by optimization of parameter 442 based on the training data including the two-dimensional data which is input data and the result of identification of object 99 which is the ground truth data. Estimation model 414 can thus generate the estimation data indicating the result of identification of object 99 included in the depth of field based on the two-dimensional data of imaged object 99.

In the practical use phase, when estimator 413 of control device 40 obtains as the geometrical data, the two-dimensional data generated based on the three-dimensional data obtained by scanning by handpiece 70, it generates the estimation data indicating the result of identification of object 99 included in the depth of field based on the obtained two-dimensional data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate object 99 included in the depth of field based on the two-dimensional data of the surface geometry of object 99 imaged by handpiece 70, and set the depth of field to the appropriate value by changing the amplitude of reciprocating motion of lens 81 based on the result of estimation.

[Pattern C]

In pattern C, the geometrical data includes the two-dimensional data, the estimation data includes data indicating the drive current to be supplied to magnetic circuitry 85, and the output data includes the drive current to be supplied to magnetic circuitry 85.

In the training phase, estimation model 414 is trained (machine trained) to estimate the estimation data based on the geometrical data, with the use of training data including the two-dimensional data included in the geometrical data and ground truth data indicating the drive current to be supplied to magnetic circuitry 85. The drive current which is the ground truth data has a value at which lens 81 makes reciprocating linear motion such that the ratio of the tooth included in the depth of field is set to the prescribed value (for example, approximately 80%) or within the prescribed range (for example, approximately 70% to approximately 90%).

Specifically, in the training phase, when estimation model 414 receives input of the two-dimensional data of imaged object 99, it extracts, with the use of neural network 441, a feature of the surface geometry of object 99 based on the two-dimensional data, and estimates the drive current to be supplied to magnetic circuitry 85 based on the extracted feature. Estimation model 414 compares the estimated drive current with the drive current included in the ground truth data. When the drive currents are equal to each other, the estimation model does not update parameter 442, whereas when the drive currents are not equal to each other, the estimation model updates parameter 442 such that they are equal to each other to optimize parameter 442. Estimation model 414 is thus machine trained by optimization of parameter 442 based on the training data including the two-dimensional data which is input data and the drive current to be supplied to magnetic circuitry 85 which is the ground truth data. Estimation model 414 can thus generate the estimation data indicating the drive current to be supplied to magnetic circuitry 85 based on the two-dimensional data of imaged object 99.

In the practical use phase, when estimator 413 of control device 40 obtains as the geometrical data, the two-dimensional data generated based on the three-dimensional data obtained by scanning by handpiece 70, it generates the estimation data indicating the drive current to be supplied to magnetic circuitry 85 based on the obtained two-dimensional data. Lens controller 412 of control device 40 outputs the drive current to be supplied to magnetic circuitry 85 as the output data to magnetic circuitry 85 based on the estimation data generated by estimator 413.

Control device 40 can thus estimate the drive current to be supplied to magnetic circuitry 85 based on the two-dimensional data of the surface geometry of object 99 imaged by handpiece 70, and set the depth of field to the appropriate value by changing the amplitude of reciprocating motion of lens 81 based on the result of estimation.

[Pattern D]

In pattern D, the geometrical data includes color data indicating a color of each point in the group of points representing the surface geometry of object 99 in addition to the two-dimensional data, the estimation data includes data indicating the ratio of the tooth in object 99 included in the current depth of field, and the output data includes the drive current to be supplied to magnetic circuitry 85.

In the training phase, estimation model 414 is trained (machine trained) to estimate the estimation data based on the geometrical data, with the use of training data including the two-dimensional data and the color data included in the geometrical data and ground truth data indicating the ratio of the tooth in object 99 included in the depth of field.

Specifically, in the training phase, when estimation model 414 receives input of the two-dimensional data and the color data of imaged object 99, it extracts a feature of the surface geometry of object 99 based on the two-dimensional data and extracts a feature of the color of the surface of object 99 based on the color data with the use of neural network 441, and estimates the ratio of the tooth in object 99 included in the depth of field based on the extracted features. Estimation model 414 compares the estimated ratio of the tooth with the ratio of the tooth included in the ground truth data.

When the ratios are equal to each other, the estimation model does not update parameter 442, whereas when the ratios are not equal to each other, the estimation model updates parameter 442 such that they are equal to each other to optimize parameter 442. Estimation model 414 is thus machine trained by optimization of parameter 442 based on the training data including the two-dimensional data and the color data which are input data and the ratio of the tooth in object 99 included in the depth of field, which is the ground truth data. Estimation model 414 can thus generate the estimation data indicating the ratio of the tooth in object 99 included in the depth of field based on the two-dimensional data and the color data of imaged object 99.

In the practical use phase, when estimator 413 of control device 40 obtains as the geometrical data, the color data and the two-dimensional data generated based on the three-dimensional data obtained by scanning by handpiece 70, it generates the estimation data indicating the ratio of the tooth in object 99 included in the depth of field based on the obtained two-dimensional data and color data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate the ratio of the tooth included in the depth of field based on the two-dimensional data and the color data of the surface geometry of object 99 imaged by handpiece 70, and set the depth of field to the appropriate value by changing the amplitude of reciprocating motion of lens 81 based on the result of estimation.

[Pattern E]

In pattern E, the geometrical data includes color data indicating a color of each point in the group of points representing the surface geometry of object 99 in addition to the two-dimensional data, the estimation data includes data indicating a result of identification of object 99 included in the current depth of field, and the output data includes the drive current to be supplied to magnetic circuitry 85.

In the training phase, estimation model 414 is trained (machine trained) to estimate the estimation data based on the geometrical data, with the use of training data including the two-dimensional data and the color data included in the geometrical data and ground truth data indicating the result of identification of object 99 included in the depth of field.

Specifically, in the training phase, when estimation model 414 receives input of the two-dimensional data and the color data of imaged object 99, it extracts a feature of the surface geometry of object 99 based on the two-dimensional data and extracts a feature of the color of the surface of object 99 based on the color data with the use of neural network 441, and identifies object 99 included in the depth of field based on the extracted features. For example, estimation model 414 specifies a portion of the tooth and a portion of the gingiva in object 99 included in the depth of field based on the two-dimensional data and the color data. Estimation model 414 compares the result of identification of object 99 with the result of identification of object 99 included in the ground truth data. When the results are equal to each other, the estimation model does not update parameter 442, whereas when the results are not equal to each other, the estimation model updates parameter 442 such that they are equal to each other to optimize parameter 442. Estimation model 414 is thus machine trained by optimization of parameter 442 based on the training data including the two-dimensional data and the color data which are input data and the result of identification of object 99 which is the ground truth data. Estimation model 414 can thus generate the estimation data indicating the result of identification of object 99 included in the depth of field based on the two-dimensional data and the color data of imaged object 99.

In the practical use phase, when estimator 413 of control device 40 obtains as the geometrical data, the color data and the two-dimensional data generated based on the three-dimensional data obtained by scanning by handpiece 70, it generates the estimation data indicating the result of identification of object 99 included in the depth of field based on the obtained two-dimensional data and color data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate object 99 included in the depth of field based on the two-dimensional data and the color data of the surface geometry of object 99 imaged by handpiece 70, and set the depth of field to the appropriate value by changing the amplitude of reciprocating motion of lens 81 based on the result of estimation.

[Pattern F]

In pattern F, the geometrical data includes color data indicating a color of each point in the group of points representing the surface geometry of object 99 in addition to the two-dimensional data, the estimation data includes data indicating the drive current to be supplied to magnetic circuitry 85, and the output data includes the drive current to be supplied to magnetic circuitry 85.

In the training phase, estimation model 414 is trained (machine trained) to estimate the estimation data based on the geometrical data, with the use of training data including the two-dimensional data and the color data included in the geometrical data and ground truth data indicating the drive current to be supplied to magnetic circuitry 85. The drive current which is the ground truth data has a value at which lens 81 makes reciprocating linear motion such that the ratio of the tooth included in the depth of field is set to the prescribed value (for example, approximately 80%) or within the prescribed range (for example, approximately 70% to approximately 90%).

Specifically, in the training phase, when estimation model 414 receives input of the two-dimensional data and the color data of imaged object 99, it extracts a feature of the surface geometry of object 99 based on the two-dimensional data and extracts a feature of the color of the surface of object 99 based on the color data with the use of neural network 441, and estimates the drive current to be supplied to magnetic circuitry 85 based on the extracted features. Estimation model 414 compares the estimated drive current with the drive current included in the ground truth data. When the drive currents are equal to each other, the estimation model does not update parameter 442, whereas when the drive currents are not equal to each other, the estimation model updates parameter 442 such that they are equal to each other to optimize parameter 442. Estimation model 414 is thus machine trained by optimization of parameter 442 based on the training data including the two-dimensional data and the color data which are input data and the drive current to be supplied to magnetic circuitry 85 which is the ground truth data. Estimation model 414 can thus generate the estimation data indicating the drive current to be supplied to magnetic circuitry 85 based on the two-dimensional data and the color data of imaged object 99.

In the practical use phase, when estimator 413 of control device 40 obtains as the geometrical data, the color data and the two-dimensional data generated based on the three-dimensional data obtained by scanning by handpiece 70, it generates the estimation data indicating the drive current to be supplied to magnetic circuitry 85 based on the obtained two-dimensional data and color data. Lens controller 412 of control device 40 outputs the drive current to be supplied to magnetic circuitry 85 as the output data to magnetic circuitry 85 based on the estimation data generated by estimator 413.

Control device 40 can thus estimate the drive current to be supplied to magnetic circuitry 85 based on the two-dimensional data and the color data of the surface geometry of object 99 imaged by handpiece 70, and set the depth of field to the appropriate value by changing the amplitude of reciprocating motion of lens 81 based on the result of estimation.

[Pattern G]

In pattern G, the geometrical data includes three-dimensional data, the estimation data includes data indicating the ratio of the tooth in object 99 included in the current depth of field, and the output data includes the drive current to be supplied to magnetic circuitry 85. The three-dimensional data included in the geometrical data is three-dimensional data obtained by scanning by handpiece 70.

In the training phase, estimation model 414 is trained (machine trained) to estimate the estimation data based on the geometrical data, with the use of training data including the three-dimensional data included in the geometrical data and ground truth data indicating the ratio of the tooth in object 99 included in the depth of field.

Specifically, in the training phase, when estimation model 414 receives input of the three-dimensional data of imaged object 99, it extracts, with the use of neural network 441, a feature of the surface geometry of object 99 based on the three-dimensional data, and estimates the ratio of the tooth in object 99 included in the depth of field based on the extracted feature. Estimation model 414 compares the estimated ratio of the tooth with the ratio of the tooth included in the ground truth data. When the ratios are equal to each other, the estimation model does not update parameter 442, whereas when the ratios are not equal to each other, the estimation model updates parameter 442 such that they are equal to each other to optimize parameter 442. Estimation model 414 is thus machine trained by optimization of parameter 442 based on the training data including the three-dimensional data which is input data and the ratio of the tooth in object 99 included in the depth of field, which is the ground truth data. Estimation model 414 can thus generate the estimation data indicating the ratio of the tooth in object 99 included in the depth of field based on the three-dimensional data of imaged object 99.

In the practical use phase, when estimator 413 of control device 40 obtains as the geometrical data, the three-dimensional data obtained by scanning by handpiece 70, it generates the estimation data indicating the ratio of the tooth in object 99 included in the depth of field based on the obtained three-dimensional data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate the ratio of the tooth included in the depth of field based on the three-dimensional data of the surface geometry of object 99 imaged by handpiece 70, and set the depth of field to the appropriate value by changing the amplitude of reciprocating motion of lens 81 based on the result of estimation.

[Pattern H]

In pattern H, the geometrical data includes three-dimensional data, the estimation data includes data indicating a result of identification of object 99 included in the current depth of field, and the output data includes the drive current to be supplied to magnetic circuitry 85.

In the training phase, estimation model 414 is trained (machine trained) to estimate the estimation data based on the geometrical data, with the use of training data including the three-dimensional data included in the geometrical data and ground truth data indicating the result of identification of object 99 included in the depth of field.

Specifically, in the training phase, when estimation model 414 receives input of the three-dimensional data of imaged object 99, it extracts, with the use of neural network 441, a feature of the surface geometry of object 99 based on the three-dimensional data, and identifies object 99 included in the depth of field based on the extracted feature. For example, estimation model 414 specifies a portion of the tooth and a portion of the gingiva in object 99 included in the depth of field based on the three-dimensional data. Estimation model 414 compares the result of identification of object 99 with the result of identification of object 99 included in the ground truth data.

When the results are equal to each other, the estimation model does not update parameter 442, whereas when the results are not equal to each other, the estimation model updates parameter 442 such that they are equal to each other to optimize parameter 442. Estimation model 414 is thus machine trained by optimization of parameter 442 based on the training data including the three-dimensional data which is input data and the result of identification of object 99 which is the ground truth data. Estimation model 414 can thus generate the estimation data indicating the result of identification of object 99 included in the depth of field based on the three-dimensional data of imaged object 99.

In the practical use phase, when estimator 413 of control device 40 obtains as the geometrical data, the three-dimensional data obtained by scanning by handpiece 70, it generates the estimation data indicating the result of identification of object 99 included in the depth of field based on the obtained three-dimensional data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate object 99 included in the depth of field based on the three-dimensional data of the surface geometry of object 99 imaged by handpiece 70, and set the depth of field to the appropriate value by changing the amplitude of reciprocating motion of lens 81 based on the result of estimation.

[Pattern I]

In pattern I, the geometrical data includes three-dimensional data, the estimation data includes data indicating the drive current to be supplied to magnetic circuitry 85, and the output data includes the drive current to be supplied to magnetic circuitry 85. In the training phase, estimation model 414 is trained (machine trained) to estimate the estimation data based on the geometrical data, with the use of training data including the three-dimensional data included in the geometrical data and ground truth data indicating the drive current to be supplied to magnetic circuitry 85. The drive current which is the ground truth data has a value at which lens 81 makes reciprocating linear motion such that the ratio of the tooth included in the depth of field is set to the prescribed value (for example, approximately 80%) or within the prescribed range (for example, approximately 70% to approximately 90%).

Specifically, in the training phase, when estimation model 414 receives input of the three-dimensional data of imaged object 99, it extracts, with the use of neural network 441, a feature of the surface geometry of object 99 based on the three-dimensional data, and estimates the drive current to be supplied to magnetic circuitry 85 based on the extracted feature. Estimation model 414 compares the estimated drive current with the drive current included in the ground truth data. When the drive currents are equal to each other, the estimation model does not update parameter 442, whereas when the drive currents are not equal to each other, the estimation model updates parameter 442 such that they are equal to each other to optimize parameter 442. Estimation model 414 is thus machine trained by optimization of parameter 442 based on the training data including the three-dimensional data which is input data and the drive current to be supplied to magnetic circuitry 85 which is the ground truth data. Estimation model 414 can thus generate the estimation data indicating the drive current to be supplied to magnetic circuitry 85 based on the three-dimensional data of imaged object 99.

In the practical use phase, when estimator 413 of control device 40 obtains as the geometrical data, the three-dimensional data obtained by scanning by handpiece 70, it generates the estimation data indicating the drive current to be supplied to magnetic circuitry 85 based on the obtained three-dimensional data. Lens controller 412 of control device 40 outputs the drive current to be supplied to magnetic circuitry 85 as the output data to magnetic circuitry 85 based on the estimation data generated by estimator 413.

Control device 40 can thus estimate the drive current to be supplied to magnetic circuitry 85 based on the three-dimensional data of the surface geometry of object 99 imaged by handpiece 70, and set the depth of field to the appropriate value by changing the amplitude of reciprocating motion of lens 81 based on the result of estimation.

[Pattern J]

In pattern J, the geometrical data includes color data indicating a color of each point in the group of points representing the surface geometry of object 99 in addition to the three-dimensional data, the estimation data includes data indicating the ratio of the tooth in object 99 included in the current depth of field, and the output data includes the drive current to be supplied to magnetic circuitry 85.

In the training phase, estimation model 414 is trained (machine trained) to estimate the estimation data based on the geometrical data, with the use of training data including the three-dimensional data and the color data included in the geometrical data and ground truth data indicating the ratio of the tooth in object 99 included in the depth of field.

Specifically, in the training phase, when estimation model 414 receives input of the three-dimensional data and the color data of imaged object 99, it extracts a feature of the surface geometry of object 99 based on the three-dimensional data and extracts a feature of the color of the surface of object 99 based on the color data with the use of neural network 441, and estimates the ratio of the tooth in object 99 included in the depth of field based on the extracted features. Estimation model 414 compares the estimated ratio of the tooth with the ratio of the tooth included in the ground truth data. When the ratios are equal to each other, the estimation model does not update parameter 442, whereas when the ratios are not equal to each other, the estimation model updates parameter 442 such that they are equal to each other to optimize parameter 442. Estimation model 414 is thus machine trained by optimization of parameter 442 based on the training data including the three-dimensional data and the color data which are input data and the ratio of the tooth in object 99 included in the depth of field, which is the ground truth data. Estimation model 414 can thus generate the estimation data indicating the ratio of the tooth in object 99 included in the depth of field based on the three-dimensional data and the color data of imaged object 99.

In the practical use phase, when estimator 413 of control device 40 obtains as the geometrical data, the three-dimensional data and the color data obtained by scanning by handpiece 70, it generates the estimation data indicating the ratio of the tooth in object 99 included in the depth of field based on the obtained three-dimensional data and color data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate the ratio of the tooth included in the depth of field based on the three-dimensional data and the color data of the surface geometry of object 99 imaged by handpiece 70, and set the depth of field to the appropriate value by changing the amplitude of reciprocating motion of lens 81 based on the result of estimation.

[Pattern K]

In pattern K, the geometrical data includes color data indicating a color of each point in the group of points representing the surface geometry of object 99 in addition to the three-dimensional data, the estimation data includes data indicating a result of identification of object 99 included in the current depth of field, and the output data includes the drive current to be supplied to magnetic circuitry 85.

In the training phase, estimation model 414 is trained (machine trained) to estimate the estimation data based on the geometrical data, with the use of training data including the three-dimensional data and the color data included in the geometrical data and ground truth data indicating the result of identification of object 99 included in the depth of field.

Specifically, in the training phase, when estimation model 414 receives input of the three-dimensional data and the color data of imaged object 99, it extracts a feature of the surface geometry of object 99 based on the three-dimensional data and extracts a feature of the color of the surface of object 99 based on the color data with the use of neural network 441, and identifies object 99 included in the depth of field based on the extracted features. For example, estimation model 414 specifies a portion of the tooth and a portion of the gingiva in object 99 included in the depth of field based on the three-dimensional data and the color data. Estimation model 414 compares the result of identification of object 99 with the result of identification of object 99 included in the ground truth data. When the results are equal to each other, the estimation model does not update parameter 442, whereas when the results are not equal to each other, the estimation model updates parameter 442 such that they are equal to each other to optimize parameter 442. Estimation model 414 is thus machine trained by optimization of parameter 442 based on the training data including the three-dimensional data and the color data which are input data and the result of identification of object 99 which is the ground truth data. Estimation model 414 can thus generate the estimation data indicating the result of identification of object 99 included in the depth of field based on the three-dimensional data and the color data of imaged object 99.

In the practical use phase, when estimator 413 of control device 40 obtains as the geometrical data, the three-dimensional data and the color data obtained by scanning by handpiece 70, it generates the estimation data indicating the result of identification of object 99 included in the depth of field based on the obtained three-dimensional data and color data. Lens controller 412 of control device 40 determines based on the estimation data generated by estimator 413, the value of the drive current to be supplied to magnetic circuitry 85 in handpiece 70 such that the ratio of the tooth included in the depth of field is set to the prescribed value (for example, approximately 80%) or within the prescribed range (for example, approximately 70% to approximately 90%) and outputs the determined drive current as the output data to magnetic circuitry 85.

Control device 40 can thus estimate object 99 included in the depth of field based on the three-dimensional data and the color data of the surface geometry of object 99 imaged by handpiece 70, and set the depth of field to the appropriate value by changing the amplitude of reciprocating motion of lens 81 based on the result of estimation.

[Pattern L]

In pattern L, the geometrical data includes color data indicating a color of each point in the group of points representing the surface geometry of object 99 in addition to the three-dimensional data, the estimation data includes data indicating the drive current to be supplied to magnetic circuitry 85, and the output data includes the drive current to be supplied to magnetic circuitry 85.

In the training phase, estimation model 414 is trained (machine trained) to estimate the estimation data based on the geometrical data, with the use of training data including the three-dimensional data and the color data included in the geometrical data and ground truth data indicating the drive current to be supplied to magnetic circuitry 85. The drive current which is the ground truth data has a value at which lens 81 makes reciprocating linear motion such that the ratio of the tooth included in the depth of field is set to the prescribed value (for example, approximately 80%) or within the prescribed range (for example, approximately 70% to approximately 90%).

Specifically, in the training phase, when estimation model 414 receives input of the three-dimensional data and the color data of imaged object 99, it extracts a feature of the surface geometry of object 99 based on the three-dimensional data and extracts a feature of the color of the surface of object 99 based on the color data with the use of neural network 441, and estimates the drive current to be supplied to magnetic circuitry 85 based on the extracted features. Estimation model 414 compares the estimated drive current with the drive current included in the ground truth data. When the drive currents are equal to each other, the estimation model does not update parameter 442, whereas when the drive currents are not equal to each other, the estimation model updates parameter 442 such that they are equal to each other to optimize parameter 442. Estimation model 414 is thus machine trained by optimization of parameter 442 based on the training data including the three-dimensional data and the color data which are input data and the drive current to be supplied to magnetic circuitry 85 which is the ground truth data. Estimation model 414 can thus generate the estimation data indicating the drive current to be supplied to magnetic circuitry 85 based on the three-dimensional data and the color data of imaged object 99.

In the practical use phase, when estimator 413 of control device 40 obtains as the geometrical data, the three-dimensional data and the color data obtained by scanning by handpiece 70, it generates the estimation data indicating the drive current to be supplied to magnetic circuitry 85 based on the obtained three-dimensional data and color data. Lens controller 412 of control device 40 outputs the drive current to be supplied to magnetic circuitry 85 as the output data to magnetic circuitry 85 based on the estimation data generated by estimator 413.

Control device 40 can thus estimate the drive current to be supplied to magnetic circuitry 85 based on the three-dimensional data and the color data of the surface geometry of object 99 imaged by handpiece 70, and set the depth of field to the appropriate value by changing the amplitude of reciprocating motion of lens 81 based on the result of estimation.

A camera for medical use that takes a picture of the inside of the mouth cavity or the inside of the outer ear or the digestive system such as the stomach or the intestines may be applicable as a medical care apparatus to which three-dimensional scanner 100 is applied. In this case, a lens of the camera may be applicable as an object to be held by a mover of the linear motor and a counterweight may be applicable as another mover.

A microscope may be applicable as a medical care apparatus to which three-dimensional scanner 100 is applied. In this case, a lens in the microscope may be applicable as an object to be held by a mover of the linear motor and a counterweight may be applicable as another mover.

Furthermore, a laser pointer that points an object such as a diagram with laser beams or a laser apparatus that cuts a tooth may be applicable as a medical care apparatus to which three-dimensional scanner 100 is applied. In this case, a lens may be applicable as an object to be held by a mover of the linear motor and a counterweight may be applicable as another mover.

It should be understood that the embodiment disclosed herein is illustrative and non-restrictive in every respect. The scope of the present disclosure is defined by the terms of the claims rather than the description above and is intended to include any modifications within the scope and meaning equivalent to the terms of the claims. Features exemplified in the embodiment and features exemplified in the modification can be combined as appropriate.

What is claimed is:

1. A three-dimensional scanner configured to obtain three-dimensional data of a surface geometry of an object with a focus method, the three-dimensional scanner comprising:
- a lens;
- imaging circuitry configured to obtain an image of the object located at a focal position of the lens;
- a lens driver configured to drive the lens to make reciprocating motion in a linear direction;
- obtaining circuitry configured to obtain geometrical data representing the surface geometry based on the image taken by the imaging circuitry;
- an estimator circuitry configured to estimate a ratio, in a depth of field, of a tooth included in the object based on the geometrical data obtained by the obtaining circuitry; and
- lens controller circuitry configured to control the lens driver to change an amplitude of reciprocating motion of the lens based on the ratio.

2. The three-dimensional scanner according to claim 1, wherein
- the estimator circuitry is further configured to estimate the ratio based on the geometrical data and a machine-trained estimation model.

3. The three-dimensional scanner according to claim 2, wherein
- the estimator circuitry is further configured to further estimate a result of identification of the object.

4. The three-dimensional scanner according to claim 1, wherein
- the lens controller circuitry is further configured to change the amplitude of reciprocating motion of the lens such that the ratio is set to a prescribed value.

5. The three-dimensional scanner according to claim 1, wherein
- the lens controller circuitry is further configured to change the amplitude of reciprocating motion of the lens such that the ratio is within a prescribed range.

6. The three-dimensional scanner according to claim 1, wherein
- the geometrical data includes two-dimensional data of the surface geometry or the three-dimensional data of the surface geometry.

7. The three-dimensional scanner according to claim 6, wherein
- the geometrical data includes data indicating a color of the object.

8. The three-dimensional scanner according to claim 1, wherein
- the imaging circuitry is configured to change a frame rate of imaging of the object in accordance with the amplitude of reciprocating motion of the lens.

9. The three-dimensional scanner according to claim 1, further comprising:
- a counterweight identical or substantially identical in mass to the lens;
- a counterweight driver configured to drive the counterweight to make reciprocating motion in a direction opposite to reciprocating motion of the lens; and
- counterweight controller circuitry configured to control an operation of the counterweight in accordance with an operation of the lens.

10. The three-dimensional scanner according to claim 1, further comprising a hand-held housing in which the lens is accommodated.

11. A control method of controlling a three-dimensional scanner configured to obtain three-dimensional data of a surface geometry of an object, the control method comprising, using processing circuitry of a computer:

obtaining an image of the object located at a focal position of a lens provided in the three-dimensional scanner;

driving the lens to make reciprocating motion in a linear direction;

obtaining geometrical data representing the surface geometry based on an image taken in the obtaining of the image;

estimating a ratio, in a depth of field, of a tooth included in the object based on the geometrical data; and changing an amplitude of reciprocating motion of the lens based on the ratio.

12. The control method according to claim 11, wherein the estimating includes estimating the ratio based on the geometrical data and a machine-trained estimation model.

13. The control method according to claim 12, wherein the estimating further includes estimating a result of identification of the object.

14. The control method according to claim 11, further comprising:

changing the amplitude of reciprocating motion of the lens such that the ratio is set to a prescribed value.

15. The control method according to claim 11, further comprising:

changing the amplitude of reciprocating motion of the lens such that the ratio is within a prescribed range.

16. The control method according to claim 11, wherein the geometrical data includes two-dimensional data of the surface geometry or the three-dimensional data of the surface geometry.

17. The control method according to claim 16, wherein the geometrical data includes data indicating a color of the object.

18. The control method according to claim 11, further comprising:

changing a frame rate of imaging of the object in accordance with the amplitude of reciprocating motion of the lens.

* * * * *